United States Patent [19]
Asai et al.

[11] Patent Number: 5,364,977
[45] Date of Patent: Nov. 15, 1994

[54] CLATHRATE COMPOUNDS COMPRISING TETRAKISPHENOLS AS HOST

[75] Inventors: Makoto Asai; Hiroshi Suzuki; Takako Ichikawa, all of Ichihara, Japan

[73] Assignee: Nippon Soda Co., LTD, Tokyo, Japan

[21] Appl. No.: 105,546

[22] Filed: Aug. 12, 1993

Related U.S. Application Data

[63] Continuation-in-part of Ser. No. 98,290, Aug. 4, 1993.

[30] Foreign Application Priority Data

Dec. 1, 1992 [JP] Japan .................................. 4-345524

[51] Int. Cl.$^5$ ......................... C07C 39/12; C07C 39/14
[52] U.S. Cl. .................................. 568/720; 568/717; 568/718; 568/719
[58] Field of Search ............... 568/720, 717, 718, 719

[56] References Cited
U.S. PATENT DOCUMENTS

| | | | |
|---|---|---|---|
| 3,239,484 | 3/1966 | Stark | 568/720 |
| 4,059,638 | 11/1977 | Krimm et al. | 568/720 |
| 5,087,766 | 2/1992 | Kanayama et al. | 568/720 |

*Primary Examiner*—Werren B. Lone
*Attorney, Agent, or Firm*—Joseph C. Mason, Jr.; George B. Oujevolk; Ronald E. Smith

[57] ABSTRACT

The present invention provides novel clathrate compounds using tetrakisphenols as host. The clathrate compounds are obtained easily and efficiently by reacting tetrakisphenols represented by the general formula [I] as host and various organic compounds such as alcohol, ether, ester, ketone, heterocyclic compounds containing nitrogen, essential oil, perfume and the like as guest under the condition of solvent-free or diluted with solvent if required.

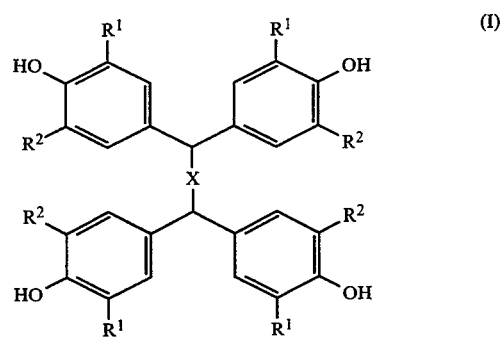

(I)

wherein X represents $(CH_2)n$, n represents 0-3, and $R^1$ and $R^2$ represents each independently hydrogen atom, a lower alkyl group, a pheny group optionally having substituents, a halogen atom or a lower alcoxy group.

The clathrate compounds specified in the present invention are useful in the technological field of selective separation, chemical stabilization, conversion to non-volatility, powder processing and the like.

11 Claims, 52 Drawing Sheets

CLATHRATE COMPOUNDS COMPRISING TETRAKISPHENOLS AS HOST

This is a continuation-in-part of copending application Ser. No. 08/098,290 filed on Aug. 4, 1993, pending.

TECHNICAL FIELD

This invention has an object to provide novel clathrate compounds which is using tetrakisphenols as host and are useful in the technological fields of selective separation, chemical stabilization, conversion to non-volatile property, powder processing and the like.

This invention also has another object to solve several problems regarding the manufacturing as described below in the conventional manufacturing process of clathrate compounds and to provide simple and efficient process for manufacturing clathrate compounds. The problems to be solved by this invention are:

1) Production of no clathrate compounds or no inclusion of guest molecule but the formation of clathrate including solvent is produced depending upon the kinds of solvents.
2) Even though the solvent is suitable to produce clathrate compounds, the conditions for the synthesis and the isolation of clathrate compounds are difficult since the conditions such as temperature, the ratio of host compound to guest compound, concentration and stirring are restricted in order to deposit the compounds including the guest molecule.
3) The recovery rate does not come to 100% on the basis of host compound.

BACKGROUND OF THE INVENTION

Clathrate compound is a compound having a structure where the guest molecules invaded into the space formed in host molecules and it is recently expected to be applied for various technological field such as selective separation, chemical stabilization, conversion to non-volatile property, powder processing and the like.

As clathrate compounds previously known, 1,1,6,6-tetraphenyl-2,4-hexazine-1,6-diol or 1,1-di(2,4-dimethylphenyl)-2-propyne-1-ol are described in Japanese Patent Laid-Open No.(Sho)61-53201(53201/1986) and 1,1'-bis-2-naphthol as host and 5-chloro-2-methyl-4-isothiazoline-3-one (CMI) as guest are described in Japanese Patent Laid-Open No. (Sho)62-2701(22701/1987).

And as the clathrate compound using tetrakisphenols as host, the one using tetrakis(4-hydroxyphenyl)ethane as host is known (See Tetrahedron Letters., 33(42),6319(1992)).

DISCLOSURE OF THE INVENTION

The inventors of the present invention and the associates found that the novel clathrate compounds are produced very efficiently by directly adding the host compound comprising specific tetrakisphenols group into the solution containing guest compound to make reaction if the guest compound is liquid, by reacting it in the solution containing guest compound if the guest compound is solid, or by direct solid-phase reaction with solid guest compound, thereby completed this invention.

The details of the present invention are illustrated hereinbelow.

Host Compounds

The host compound comprising tetrakisphenol used in the present invention is a compound represented by the general formula [I].

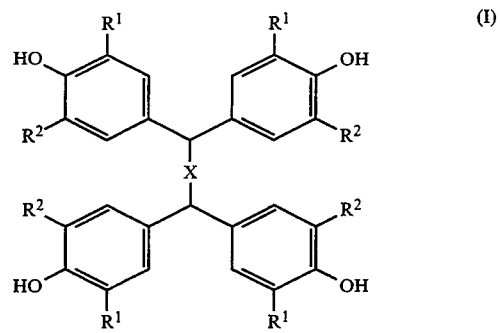

wherein X represents $(CH_2)n$, n is 1, 2 or 3, $R^1$ and $R^2$ represent each independently hydrogen, lower alkyl, unsubstituted or substituted phenyl, halogen or lower alkoxy.

$R^1$ and $R^2$ in the general formula [I] are identical or different and are, for example, hydrogen, lower alkyl such as methyl, ethyl, propyl, isopropyl, n-butyl, isobutyl, tert-butyl, n-hexyl and cyclohexyl, phenyl which is unsubstituted or substituted by halogen, lower alkyl or the like, halogen such as fluorine, chlorine, bromine and iodine, or lower alkoxy such as methoxy, ethoxy and tert-butoxy.

The tetrakisphenols used in the present invention are not particularly restricted as far as it is one of the compound represented by the general formula [I]. The following compounds are included in the tetrakis phenols as examples. 1,1,2,2-tetrakis(4-hydroxyphenyl)ethane, 1,1,2,2-tetrakis(3-methyl-4-hydroxyphenyl)ethane, 1,1,2,2-tetrakis(3,5-dimethyl-4-hydroxyphenyl) ethane, 1,1,2,2-tetrakis(3-chloro-4-hydroxyphenyl)ethane, 1,1,2,2-tetrakis(3,5-dichloro-4-hydroxyphenyl)ethane, 1,1,2,2-tetrakis(3-bromo- 4-hydroxyphenyl)ethane, 1,1,2,2-(3,5-dibromo-4-hydroxyphenyl)ethane, 1,1,2,2-tetrakis(3-tert-butyl-4-hydroxyphenyl)ethane, 1,1,2,2-tetrakis(3,5-ditert-butyl-4-hydroxyphenyl)ethane, 1,1,2,2-tetrakis(3-fluoro-4-hydroxyphenyl)ethane, 1,1,2,2-tetrakis(3,5-difluoro-4-hydroxyphenyl) ethane, 1,1,2,2-tetrakis(3-methoxy-4-hydroxyphenyl)ethane, 1,1,2,2-tetrakis(3,5-dimethoxy-4-hydroxyphenyl)ethane, 1,1,2,2-tetrakis(3-chloro-5-methyl-4-hydroxyphenyl)ethane, 1,1,2,2-tetrakis(3-bromo-5-methyl-4-hydroxyphenyl)ethane, 1,1,2,2-tetrakis(3-methoxy-5-methyl-4-hydroxyphenyl)ethane, 1,1,2,2-tetrakis(3-tert-butyl-5-methyl-4'-hydroxyphenyl)ethane, 1,1,2,2-tetrakis(3-chloro-5-bromo-4-hydroxyphenyl) ethane, 1,1,2,2-tetrakis(3-chloro-5-phenyl-4-hydroxyphenyl)ethane, 1,1,2,2-tetrakis[(4-hydroxy-3-phenyl)phenyl]ethane, 1,1,3,3-tetrakis(4-hydroxyphenyl)propane, 1,1,3,3-tetrakis(3-methyl-4-hydroxyphenyl)propane, 1,1,3,3-tetrakis(3,5-dimethyl-4-hydroxyphenyl)propane, 1,1,3,3-tetrakis(3-chloro-4-hydroxyphenyl)propane, 1,1,3,3-tetrakis(3,5-dichloro-4-hydroxyphenyl)propane, 1,1,3,3-tetrakis(3-bromo-4-hydroxyphenyl)propane, 1,1,3,3-tetrakis(3,5-dibromo-4-hydroxyphenyl) propane, 1,1,3,3-tetrakis(3-phenyl-4-hydroxyphenyl)propane, 1,1,3,3-tetrakis(3,5-diphenyl-4-hydroxyphenyl)propane, 1,1,3,3-tetrakis(3-methoxy-4-hydroxyphenyl)propane, 1,1,3,3-tetrakis(3,5-dimethoxy-4-hydroxyphenyl)propane, 1,1,3,3-tetrakis(3-tert-butyl-4-hydroxyphenyl) propane, 1,1,4,4-tetrakis(3,5-ditert-butyl-4-hydroxyphenyl)butane, 1,1,5,5-tetrakis(4-hydroxyphenyl)pentane, 1,1,5,5-tetrakis(3-methyl-4-hydroxyphenyl)pentane, 1,1,5,5-tetrakis(3,5-dimethyl-4-hydroxyphenyl) pentane. 1,1,5,5-tetrakis(3-chloro-4-hydroxyphenyl)pentane, 1,1,5,5-tetrakis(3,5-dichloro-4-hydroxyphenyl)pentane, 1,1,5,5-tetrakis(3-bromo-4-hydroxyphenyl)pentane. 1,1,5,5-tetrakis(3,5-dibromo-4-hydroxyphenyl)pentane, 1,1,5,5-tetrakis(3-methoxy-4-hydroxyphenyl) pentane, 1,1,5,5-tetrakis(3,5-dimethoxy-4-hydroxyphenyl)pentane, 1,1,5,5-tetrakis(3-tert-butyl-4-hydroxyphenyl)pentane. 1,1,5,5-tetrakis(3,5-ditert-butyl-4-hydroxyphenyl)pentane, 1,1,5,5-tetrakis(3-methyl-5-tert-butyl-4-hydroxyphenyl)pentane. 1,1,5,5-tetrakis(3-phenyl-4-hydroxyphenyl)pentane, 1,1,5,5-tetrakis(3,5-diphenyl-4-hydroxyphenyl) pentane, 1,1,5,5-tetrakis(3,5-dicyclohexyl-4-hydroxyphenyl)pentane, 1,1,4,4-tetrakis(4-hydroxyphenyl)butane, 1,1,4,4-tetrakis(3-methyl-4-hydroxyphenyl)butane, 1,1,4,4-tetrakis(3.5-dimethyl-4-hydroxyphenyl) butane, 1,1,4,4-tetrakis(3-chloro-4-hydroxyphenyl)butane, 1,1,4,4-tetrakis(3,5-dichloro-4-hydroxyphenyl)butane. 1,1,4,4-tetrakis(3-methoxy-4-hydroxyphenyl)butane, 1,1,4,4-tetrakis(3,5-dimethoxy-4-hydroxyphenyl)butane, 1,1,4,4-tetrakis(3-bromo-4-hydroxyphenyl)butane and 1,1,4,4-tetrakis(3,5-dibromo-4-hydroxyphenyl)butane.

Guest Compounds

The organic compounds enabling to form clathrate compounds of which host compound comprising tetrakisphenol can be used as the guest organic compound of the present invention without particular restriction. Examples of the above guest organic compounds are alcohols such as methanol, ethanol, i-propanol, n-butanol, 2-ethylhexanol and the like; aldehydes such as formaldehyde, acetaldehyde, benzaldehyde and the like; ketones such as acetone, methylethylketone and the like; nitriles such as acetonitrile and the like; ethers such as tetrahydrofuran, diethylether and the like; esters such as methyl acetate, ethyl acetate, butyl acetate and the like; natural essential oils such as cineole, hinokithiol, menthol, terpineol, borncol, nopol, citral, citrinellol, citronellal, geraniol, linalool, dimethyloctanol and the like; synthetic perfumes such as fragrant orange-colored olive, jasmine, lemon oil and the like; monocyclic nitrogen-containing heterocyclic compounds such as pyridine, pyrrole, imidazole, pyrazine, pyrazole, 1,2,4-triazole, thiazole, pyrrolidine, imidazoline, pyrroline, oxazole, piperine, pyrimidine, pyridazine, triazine, 5-chloro-2-methyl-4-isothiazoline-3-one and the like.

The compound of the present invention can be obtained as novel clathrate compound by reacting the said guest organic compound or the solution containing the guest organic compound with tetrakisphenol being host compound with stirring for several minutes to several hours in the temperature range from room temperature to 100° C. to include the guest organic compound into the host compound easily.

The said clathrate compound can be utilized for the separation and the recovery of guest compounds from the solution in water based on the characteristics that the clathrate compounds easily release the guest compound when heated under reduced pressure and the host compound does not include water.

According to the present invention, when the guest compound is liquid, the clathrate compound can be produced with high selectivity and high yields by directly reacting the guest compound with powdered host compound.

On the other hand, when the guest compound is solid, the clathrate compound is also produced with high selectivily and high yields by reacting the solution or the solid of the guest compound with the powdered host compound.

The clathrate compounds of the present invention result from the invasion of the molecules of the guest compound into a hollow formed by the host compound molecules. Therefore, the degree that the compound is taken into the host compound as the guest compound depends on the size, the steric structure, the polarity and the solubility of the molecules of the guest compound.

BEST MODE FOR CARRYING OUT THE INVENTION

The present invention is illustrated in more detail by the following Examples. However, the scope of the present invention should not be limited by those Examples.

All samples A-1 through A-67 obtained in the Examples were confirmed as those are desired clathrate compounds by the analytical means such as infrared spectrum, NMR spectrum, DTA, X-ray diffraction and the like.

Figure 1:
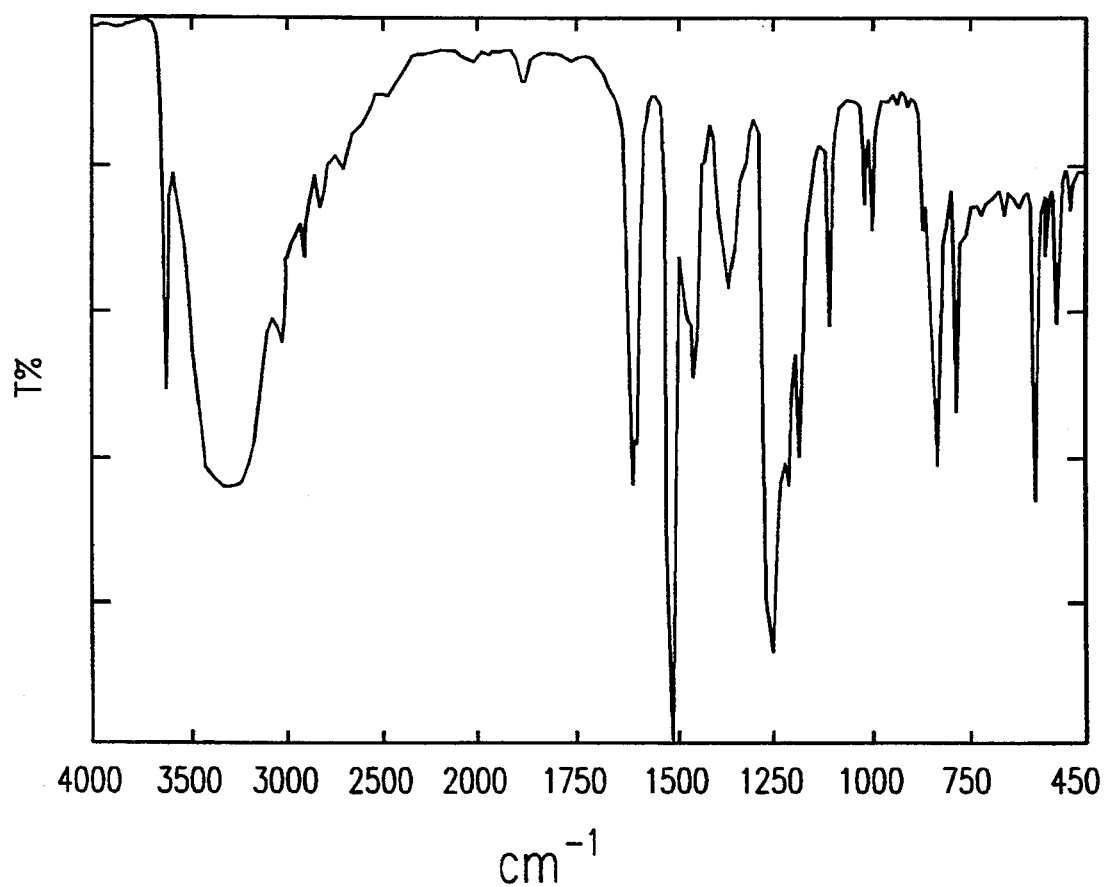
FIG. 1 is an infrared spectrum of the sample A-1.
Figure 2:
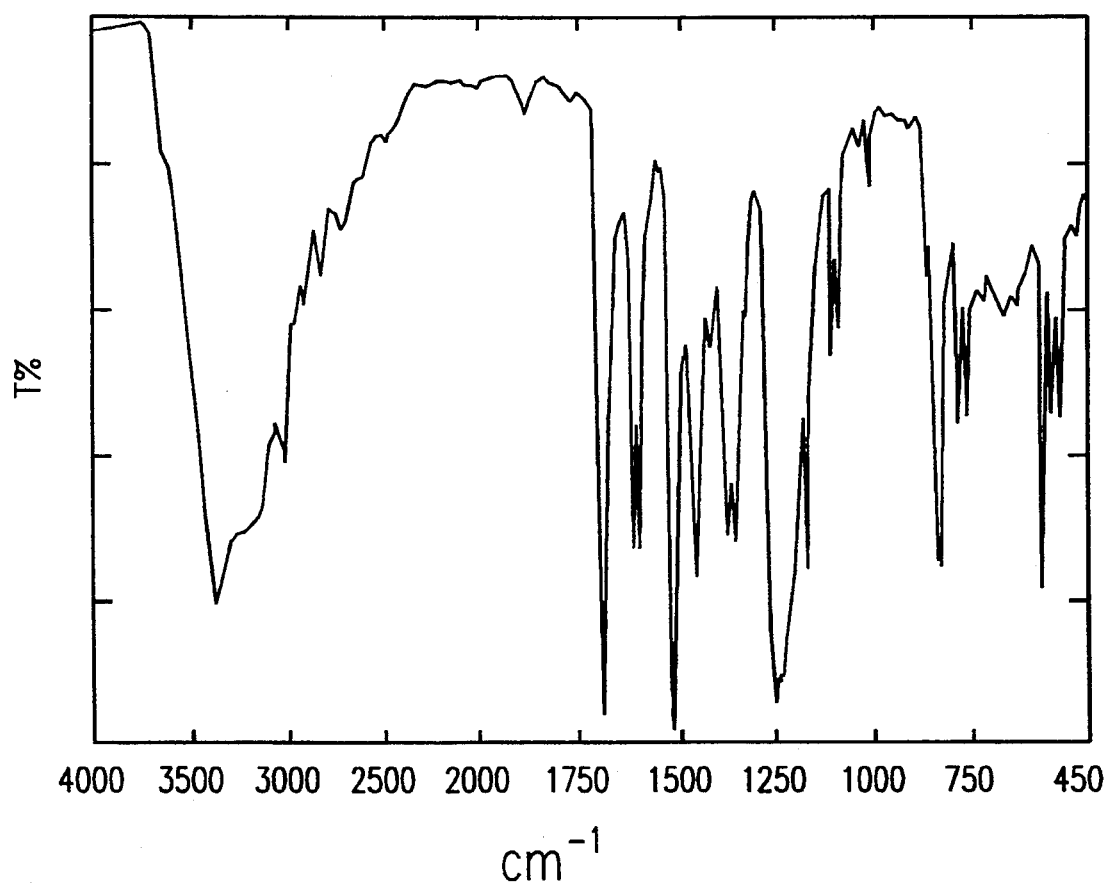
FIG. 2 is an infrared spectrum of the sample A-7.
Figure 3:
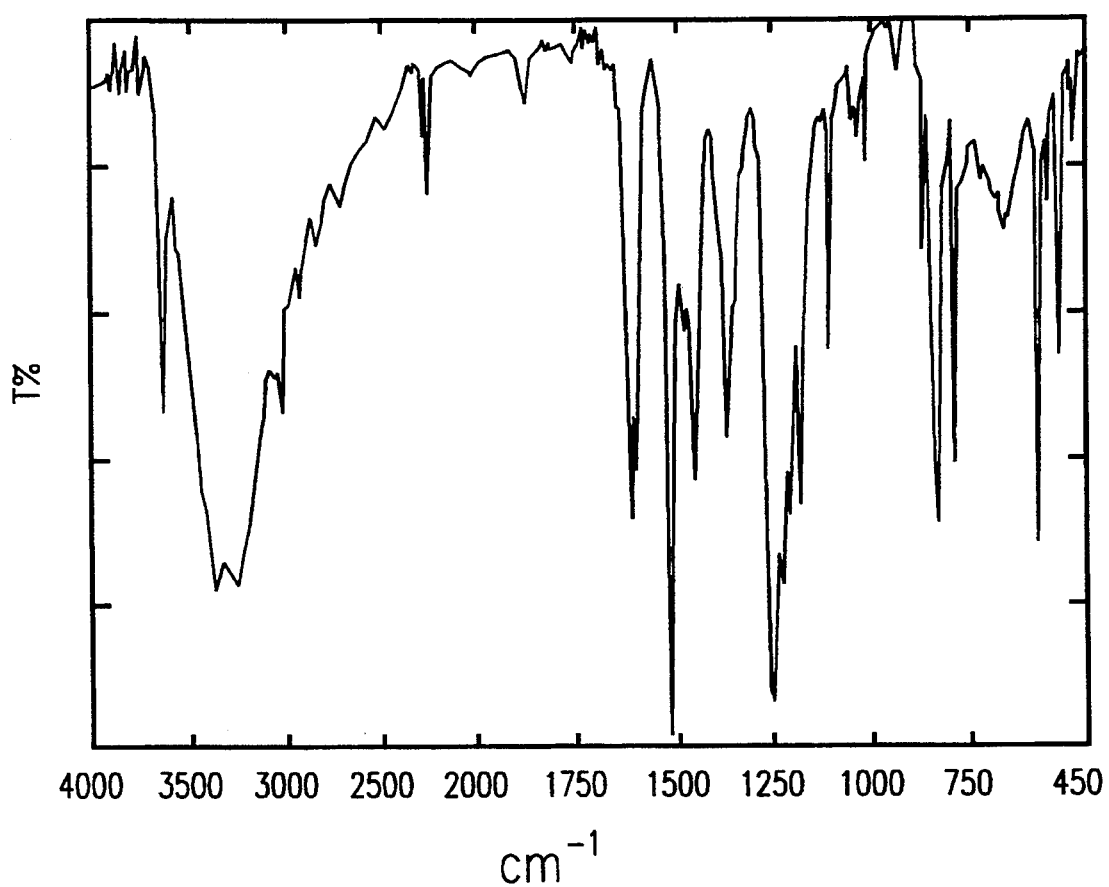
FIG. 3 is an infrared spectrum of the sample A-10.
Figure 4:
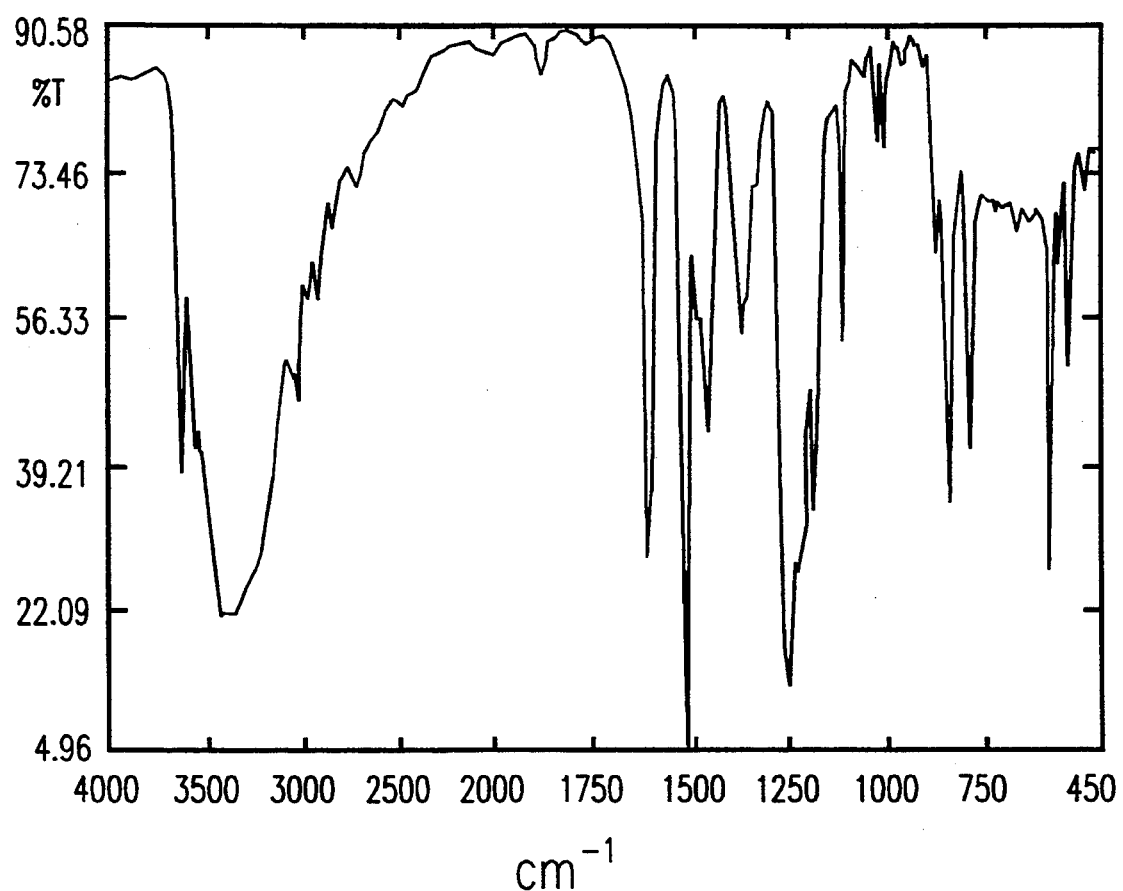
FIG. 4 is an infrared spectrum of the sample A-12.
Figure 5:
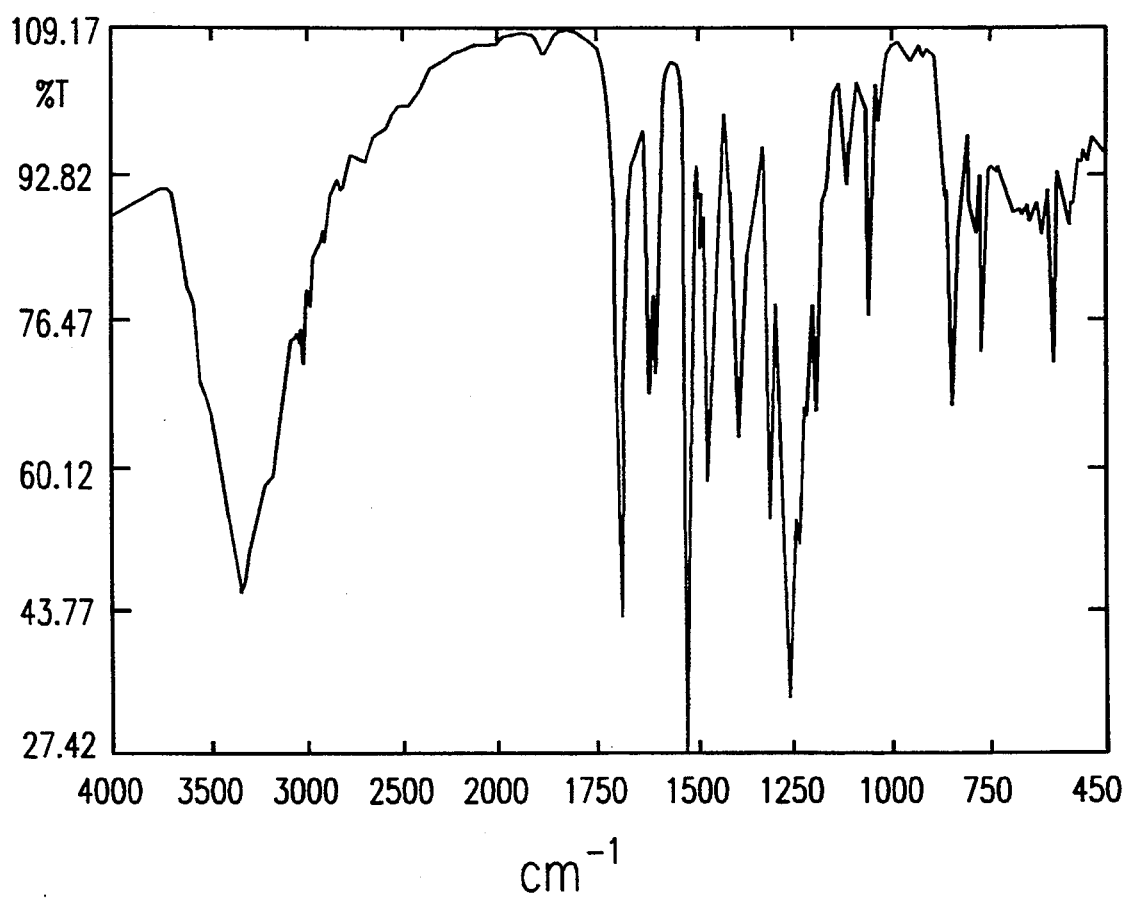
FIG. 5 is an infrared spectrum of the sample A-13.
Figure 6:
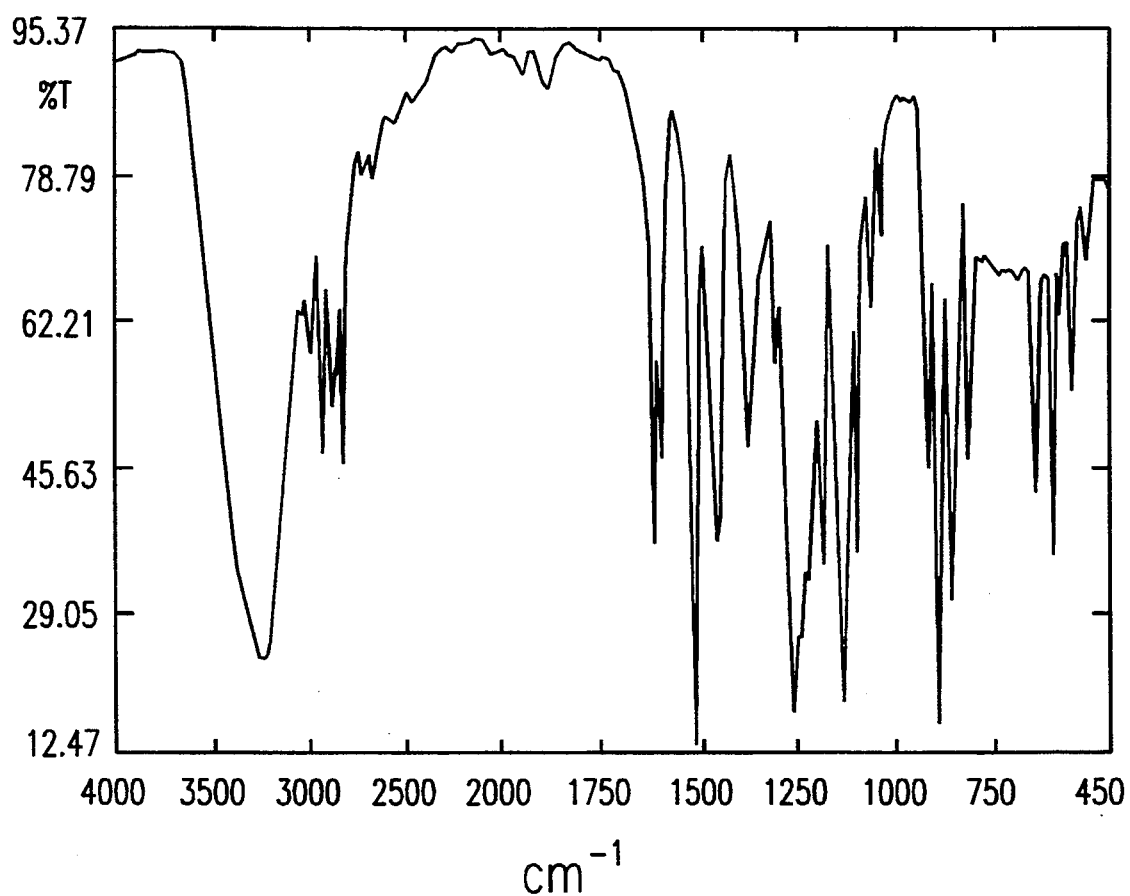
FIG. 6 is an infrared spectrum of the sample A-14.
Figure 7:
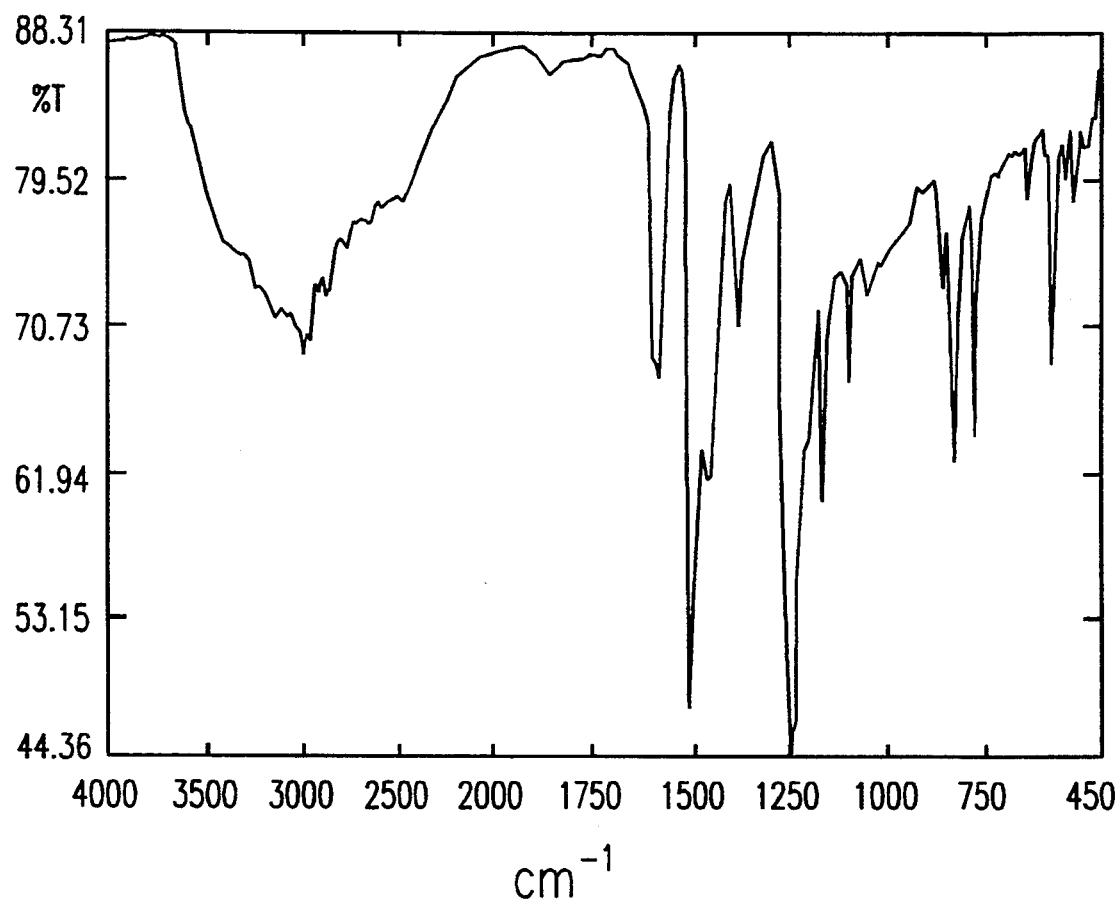
FIG. 7 is an infrared spectrum of the sample A-15.
Figure 8:
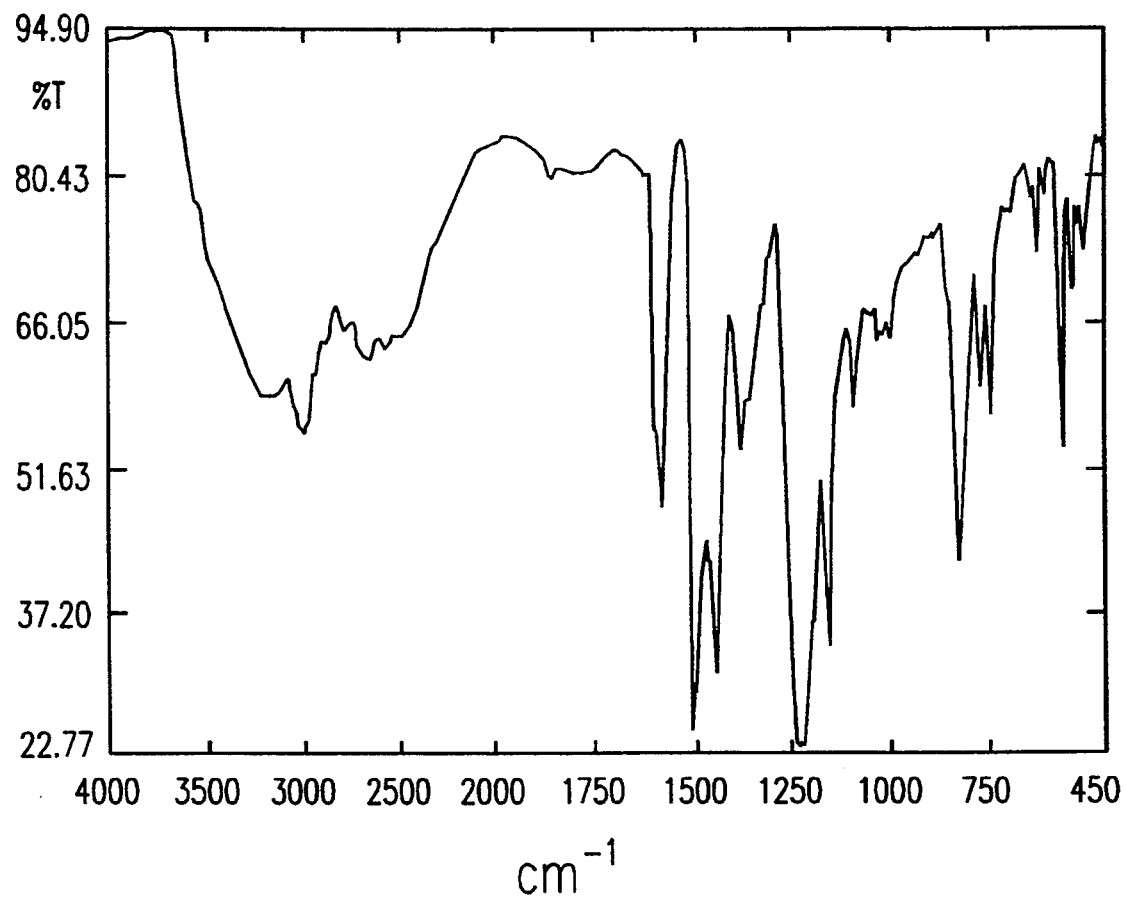
FIG. 8 is an infrared spectrum of the sample A-16.
Figure 9:
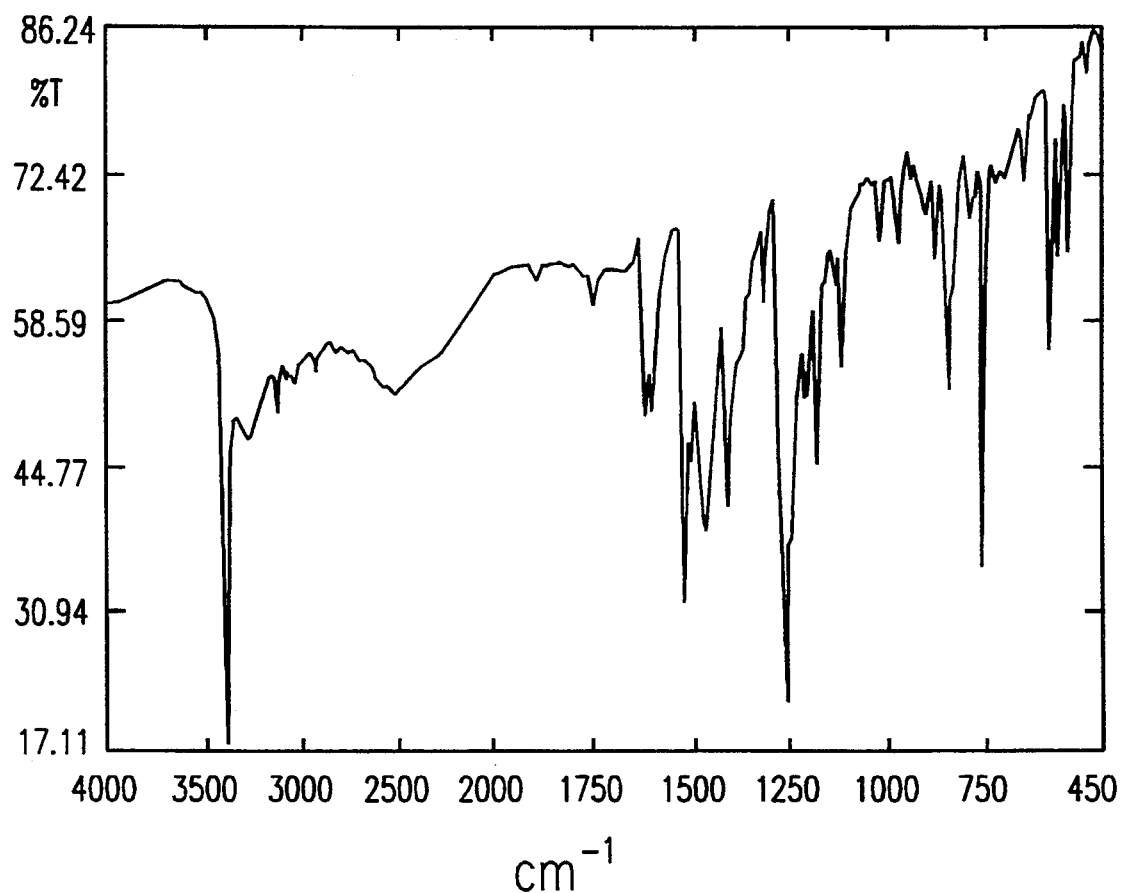
FIG. 9 is an infrared spectrum of the sample A-17.
Figure 10:
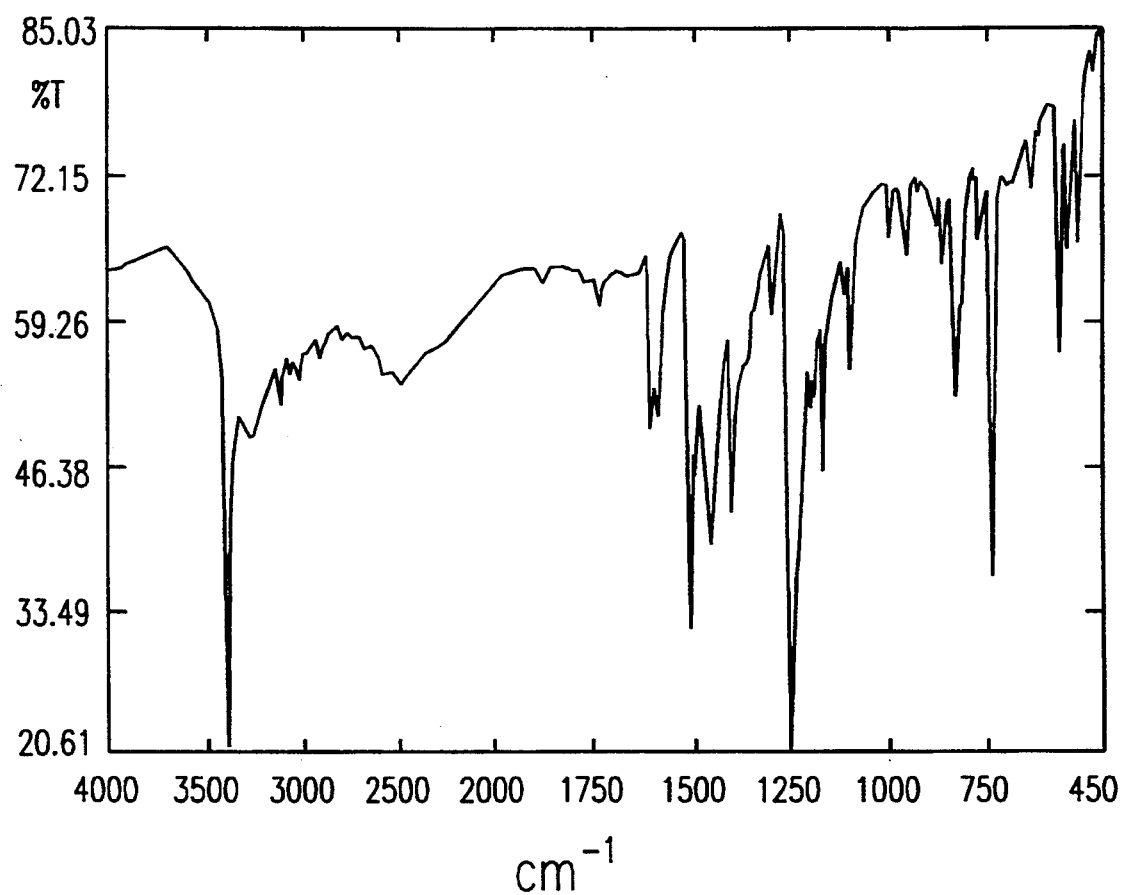
FIG. 10 is an infrared spectrum of the sample A-18.
Figure 11:
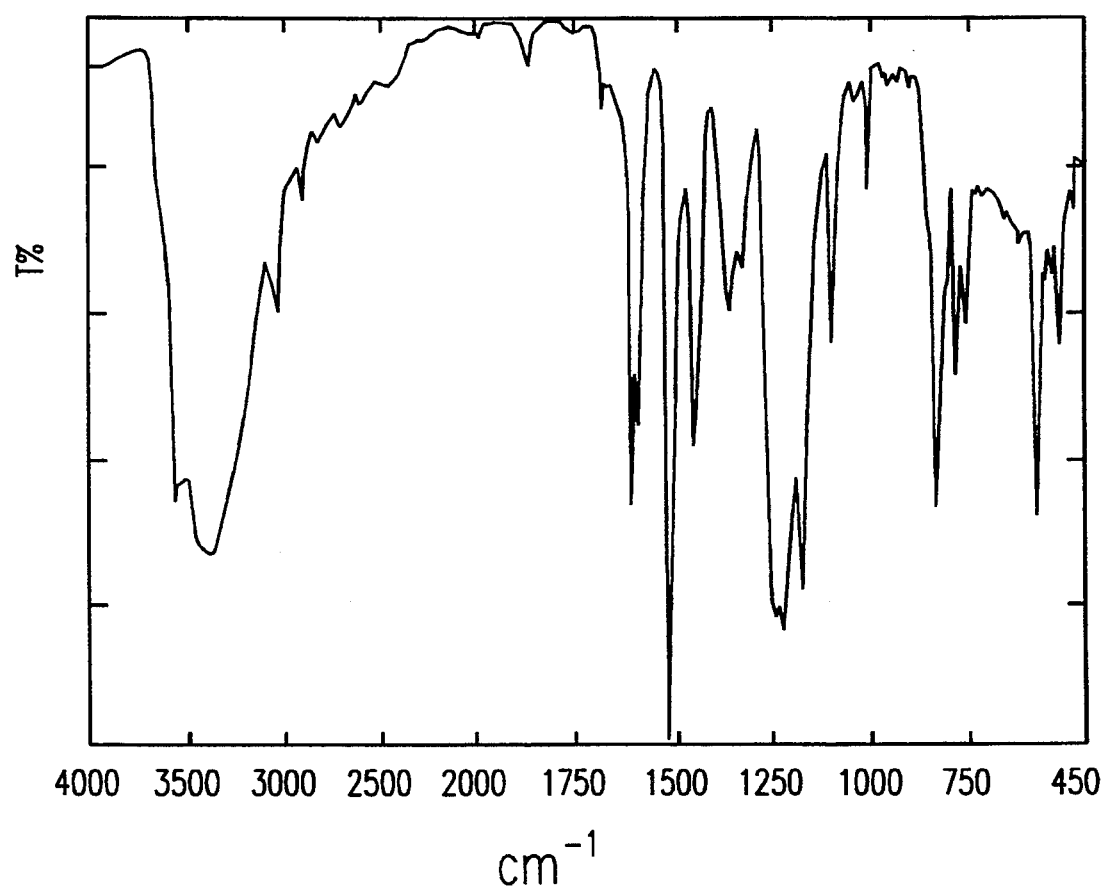
FIG. 11 is an infrared spectrum of host compound, 1,1,2,2-tetrakis(4-hydroxyphenyl)ethane (hereinafter abbreviated to TEP-DF).
Figure 12:
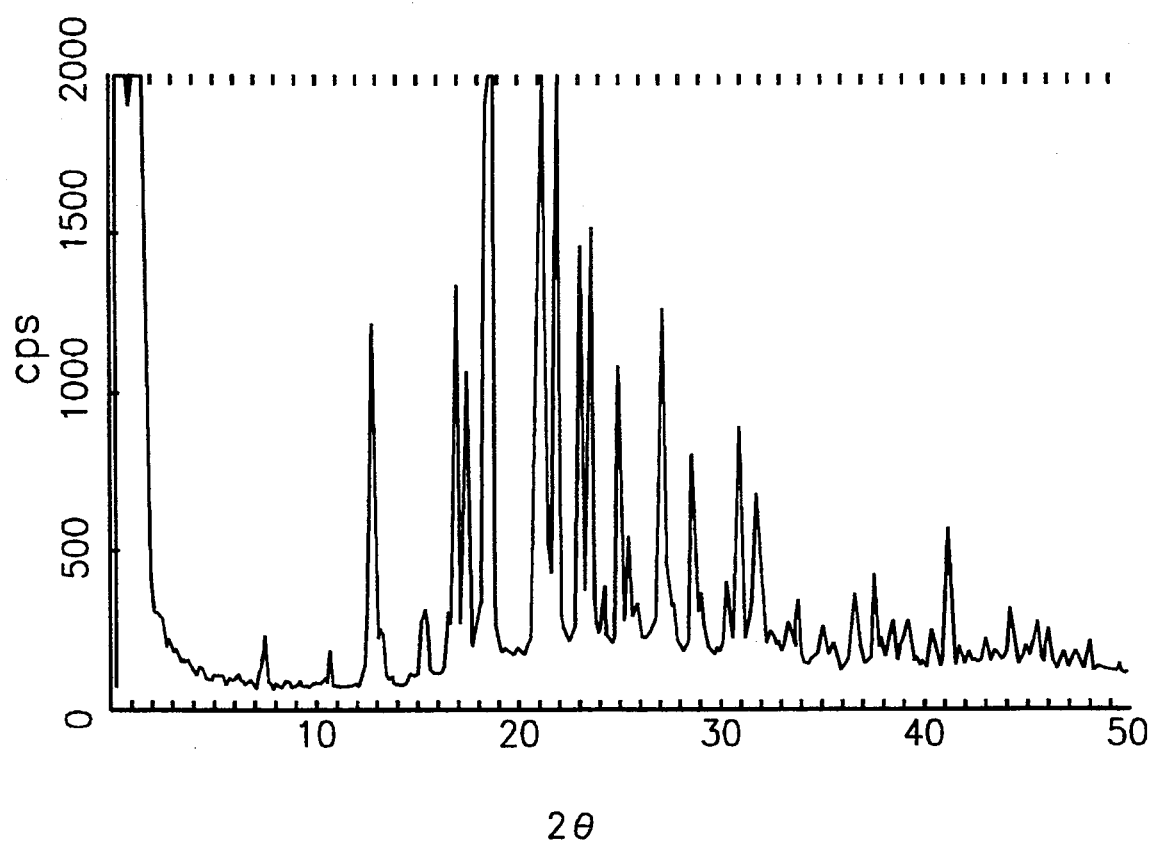
FIG. 12 is a X-ray diffraction diagram of the sample A-1.
Figure 13:
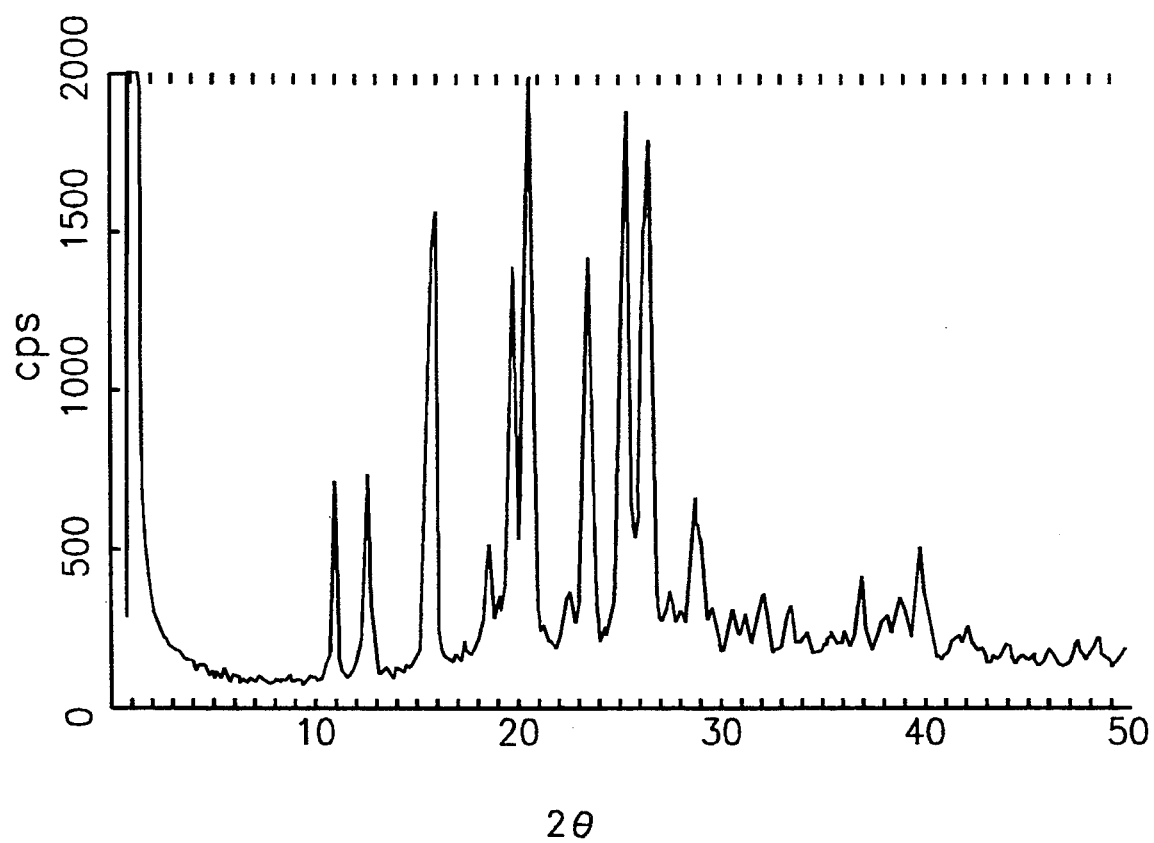
FIG. 13 is a X-ray diffraction diagram of the sample A-7.
Figure 14:
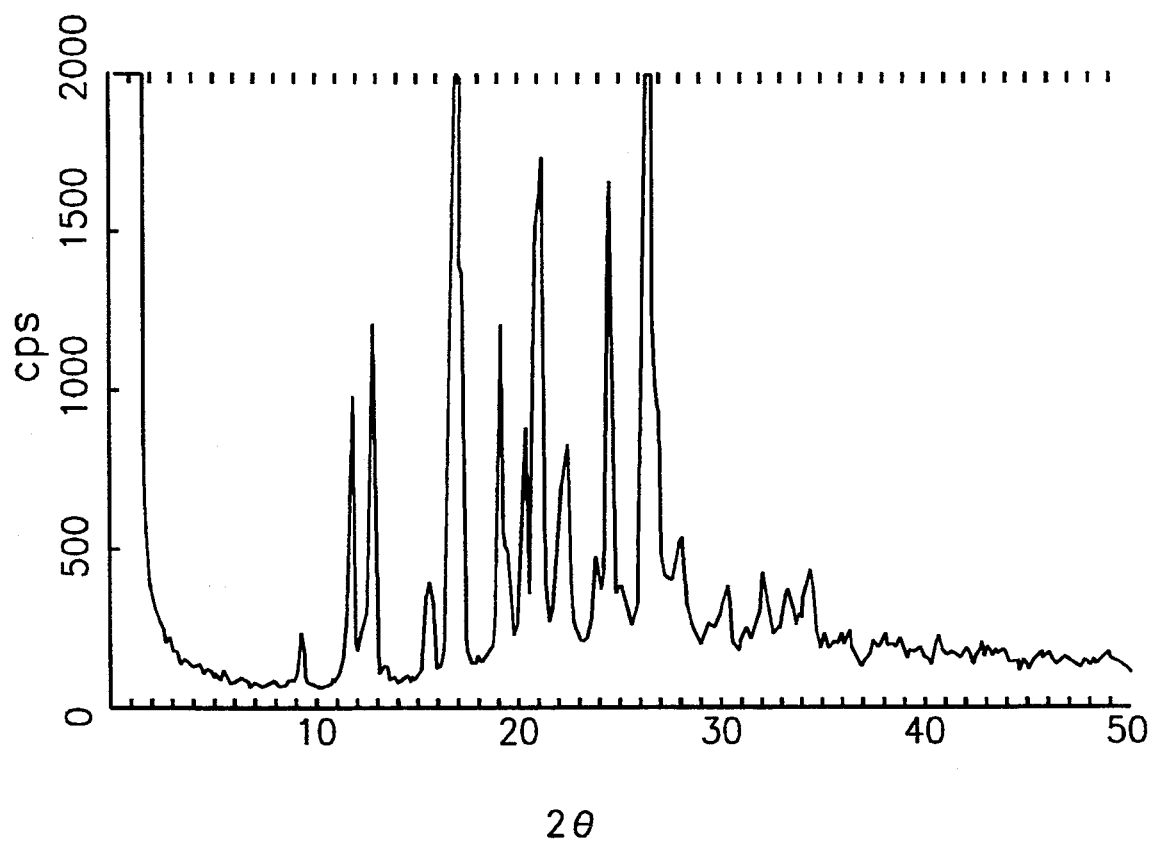
FIG. 14 is a X-ray diffraction diagram of the sample A-10.
Figure 15:
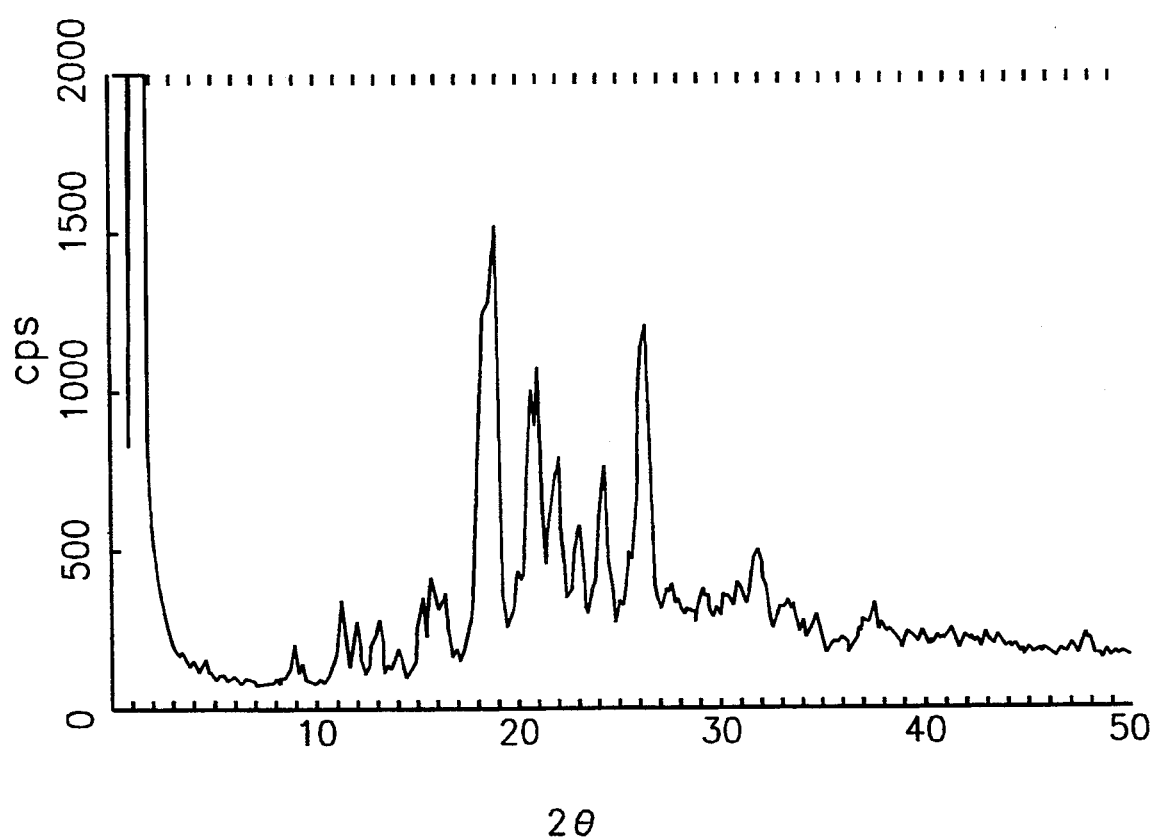
FIG. 15 is a X-ray diffraction diagram of TEP-DF.
Figure 16:
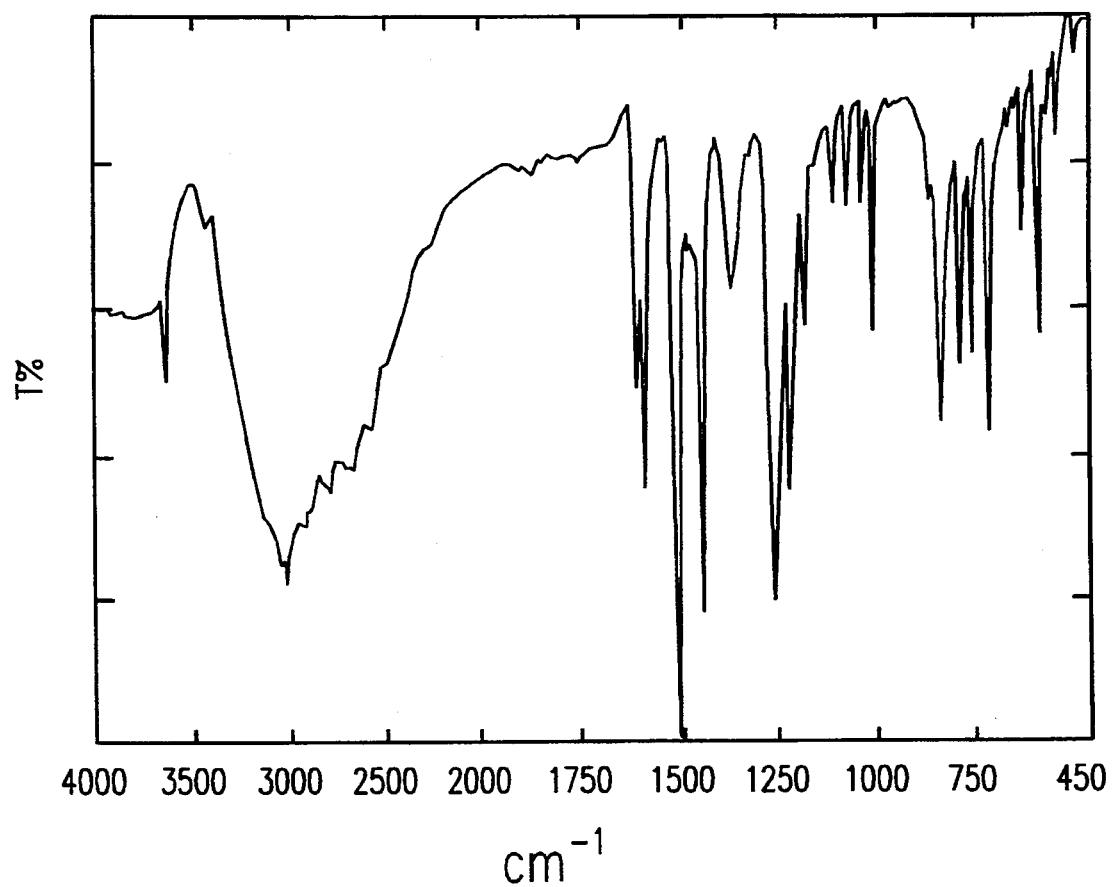
FIG. 16 is an infrared spectrum of the sample A-19.
Figure 17:
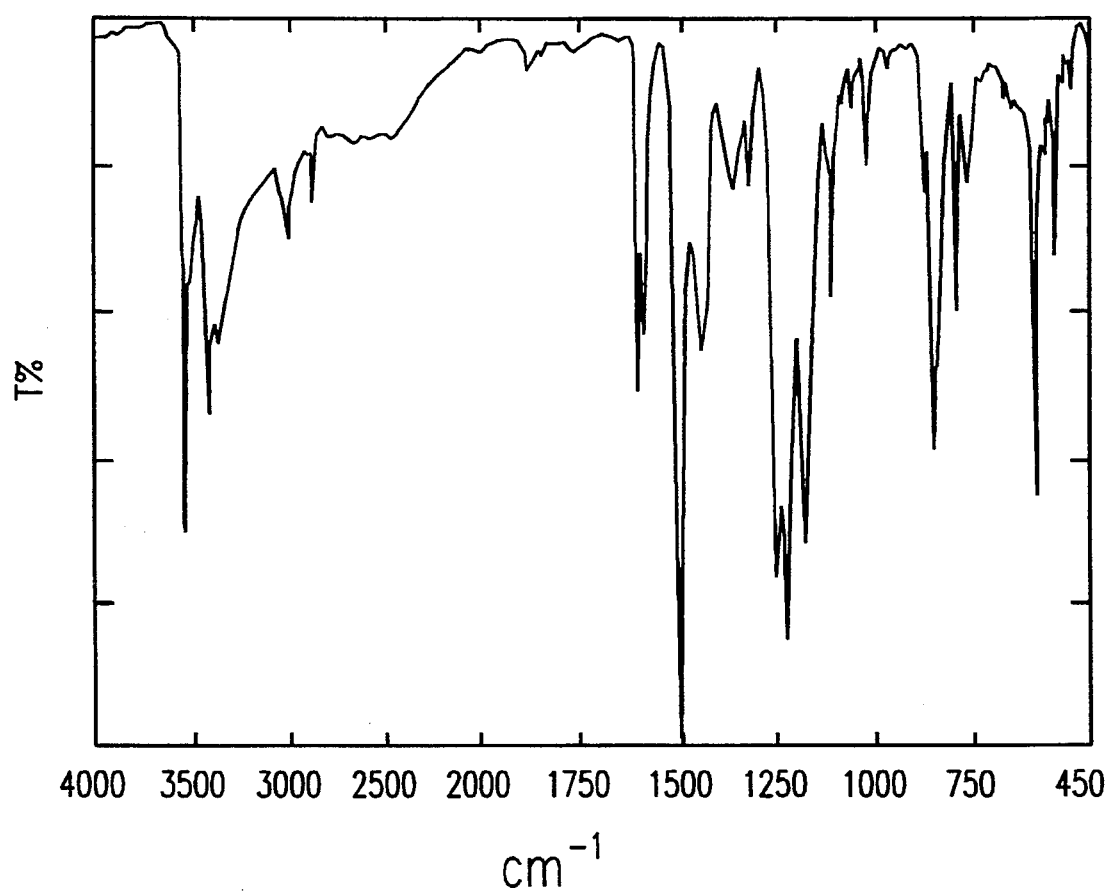
FIG. 17 is an infrared spectrum of the sample A-20.
Figure 18:
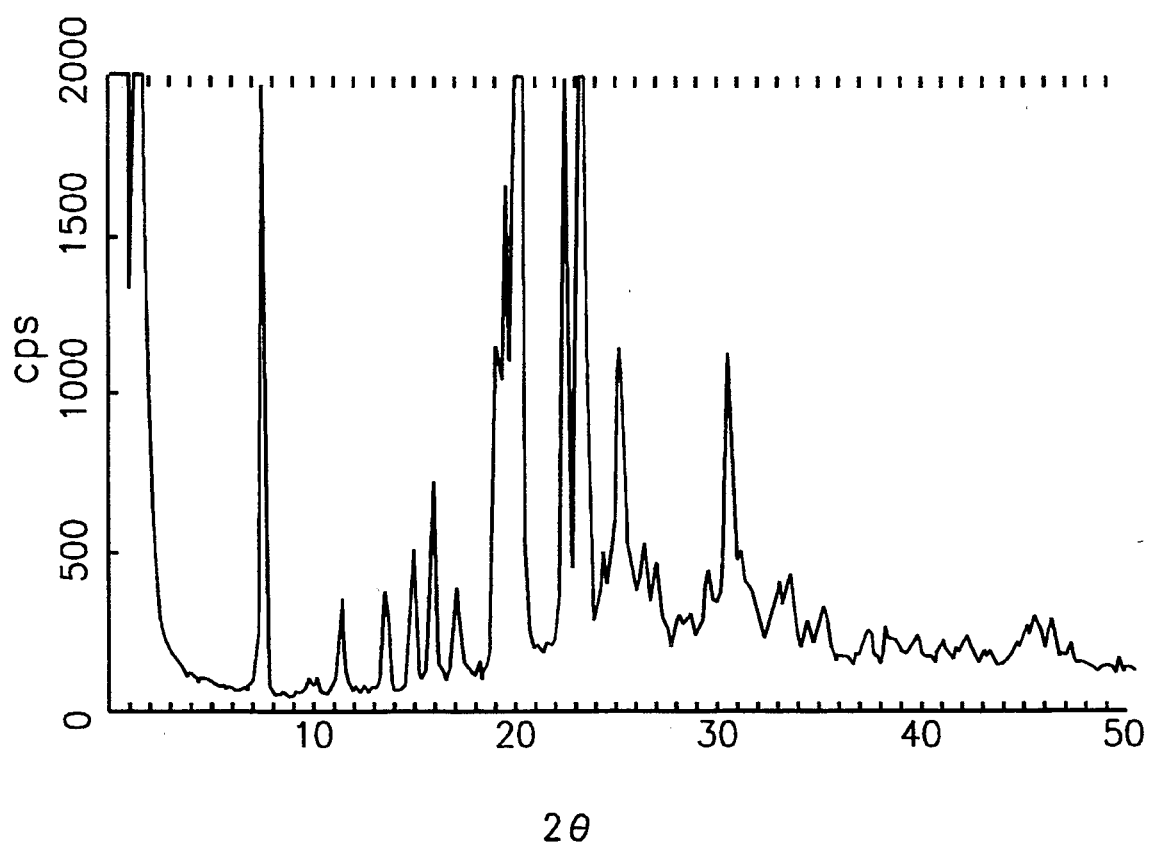
FIG. 18 is a X-ray diffraction diagram of the sample of A-19.
Figure 19:
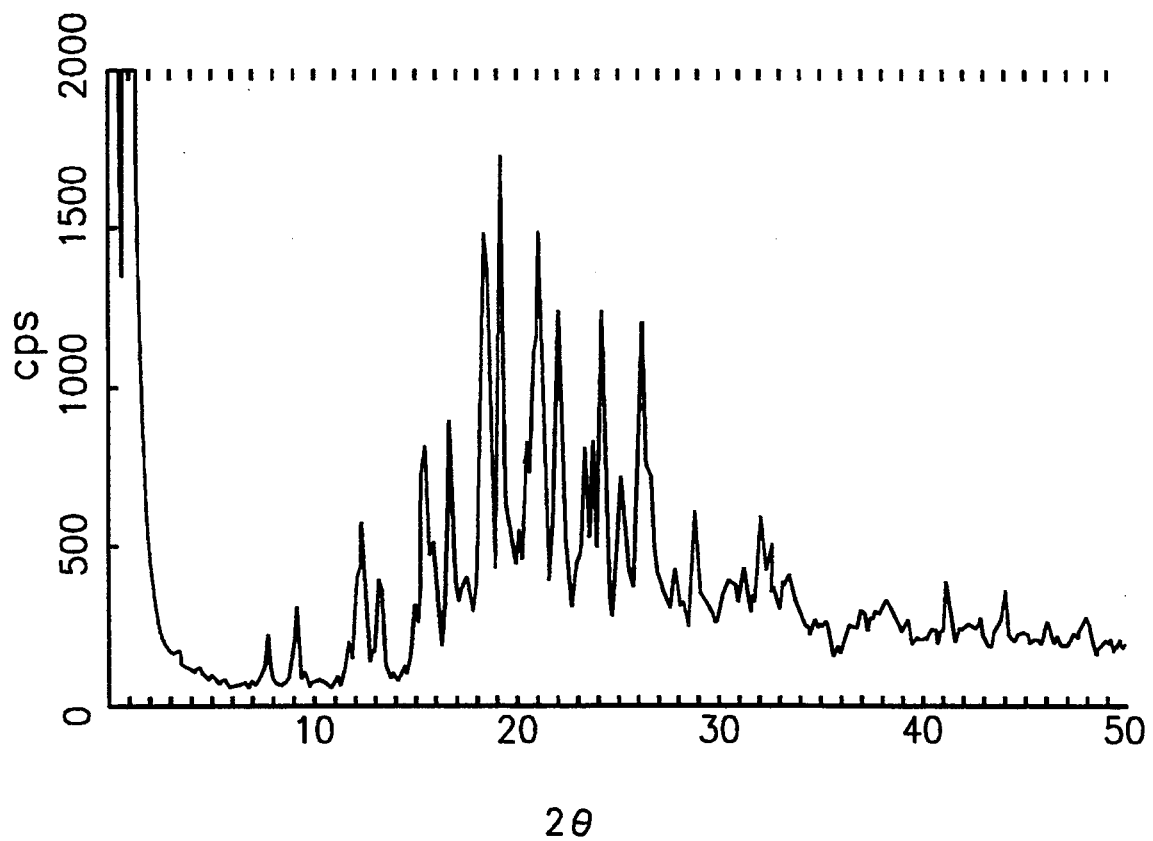
FIG. 19 is a X-ray diffraction diagram of the sample of A-20.
Figure 20:
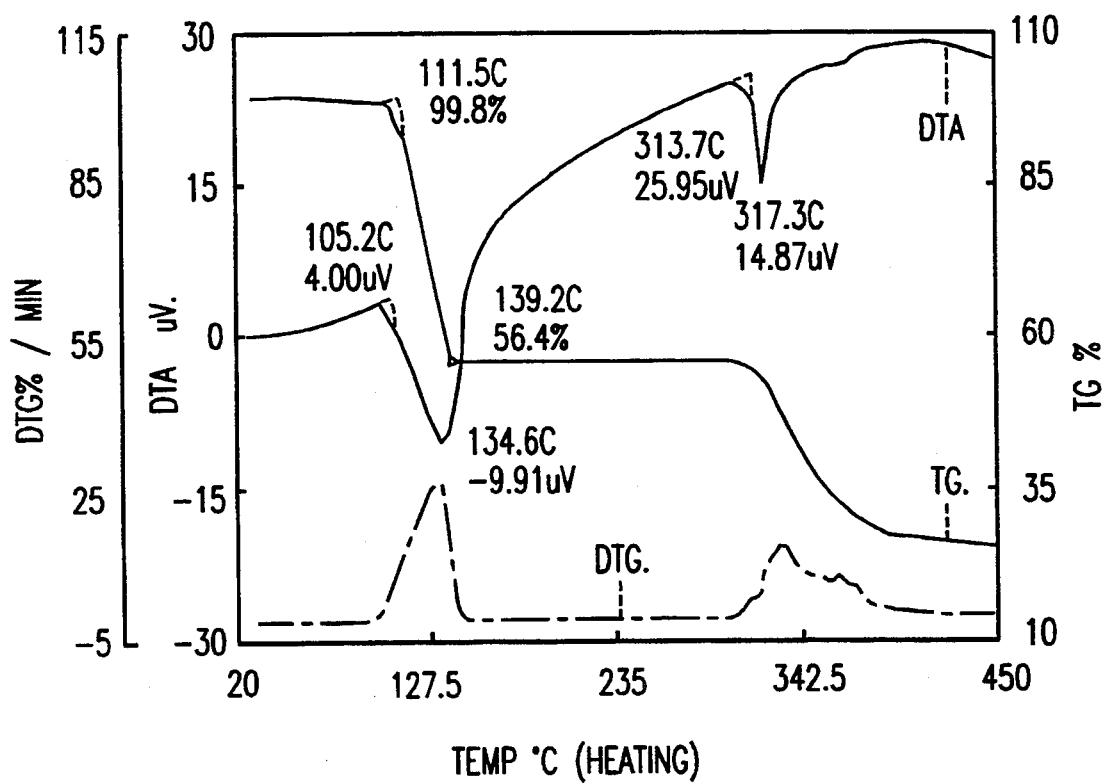
FIG. 20 is a TG/DTA chart of the sample A-19.
Figure 21:
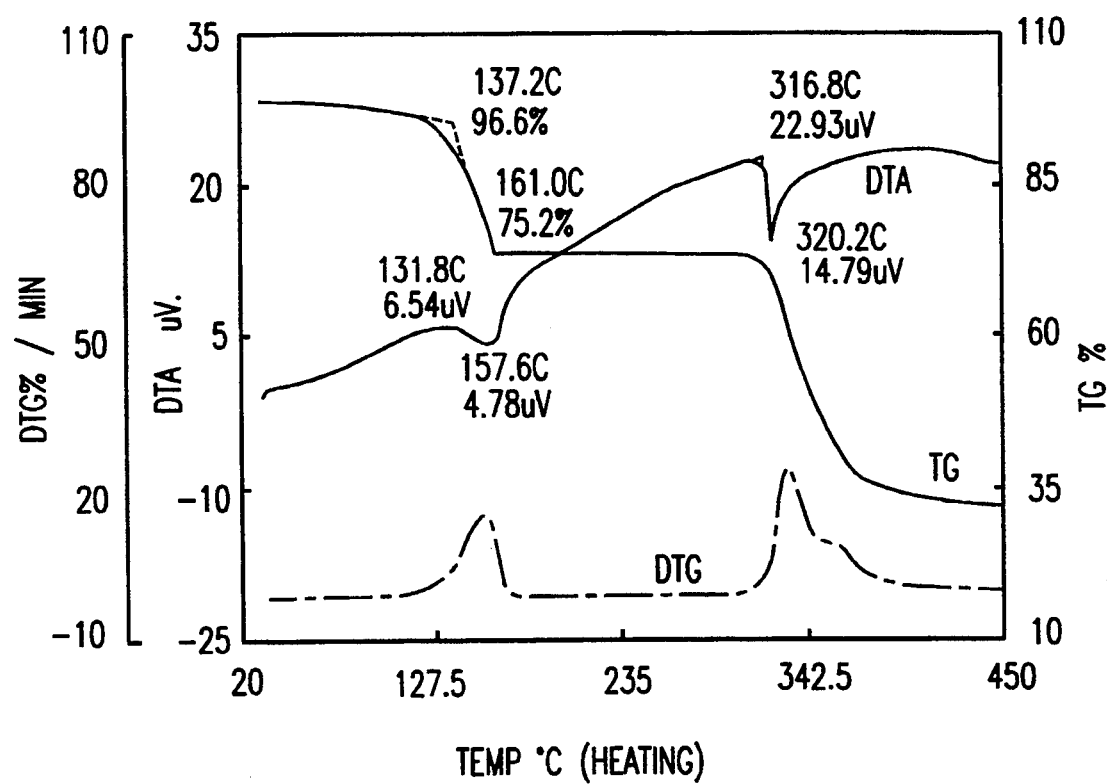
FIG. 21 is a TG/DTA chart of the sample A-20.
Figure 22:
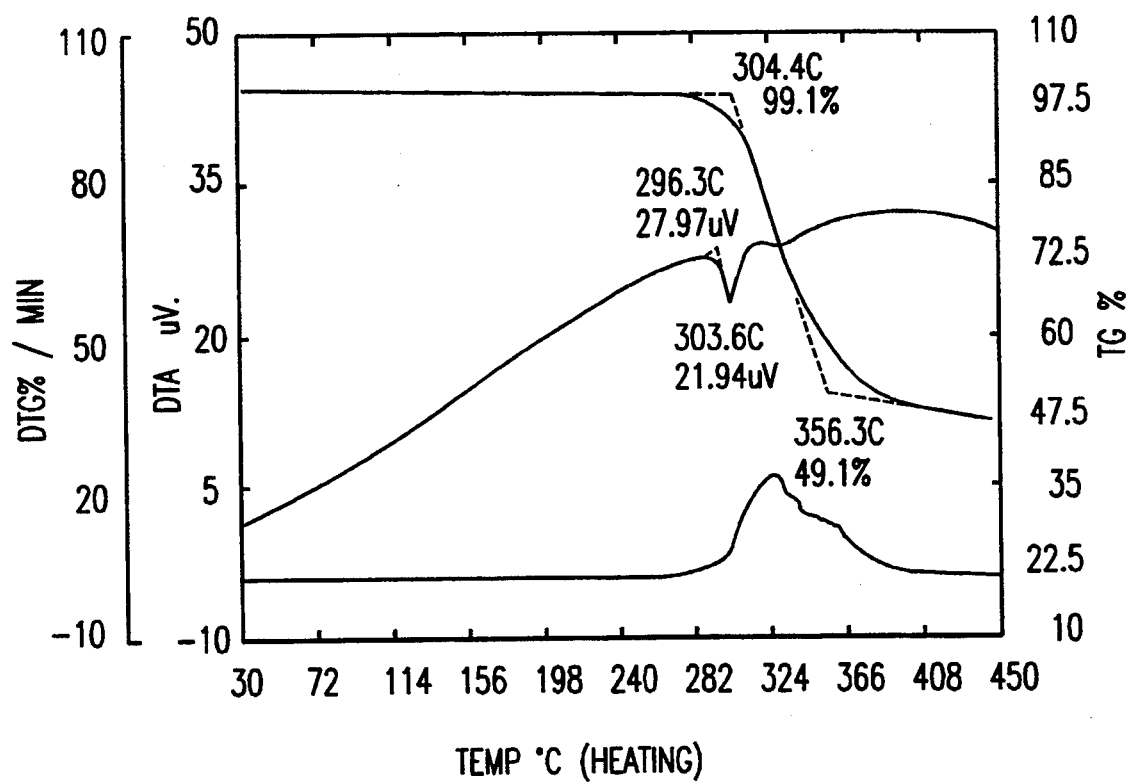
FIG. 22 is a TG/DTA chart of TEP-DF.
Figure 23:
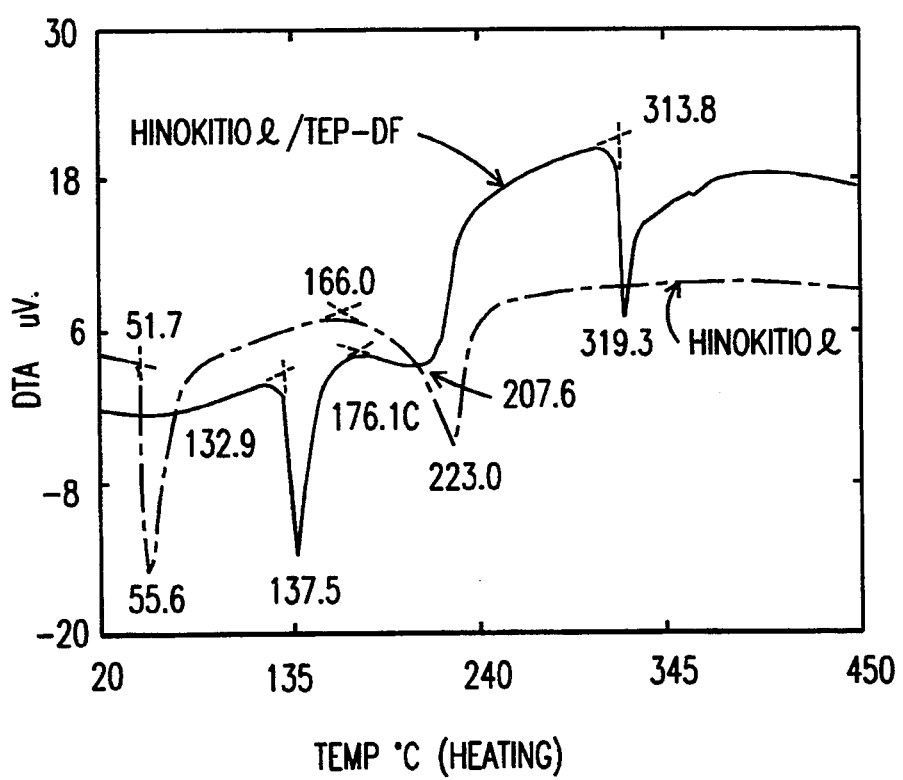
FIG. 23 is a DTA chart of the sample A-29.
Figure 24:
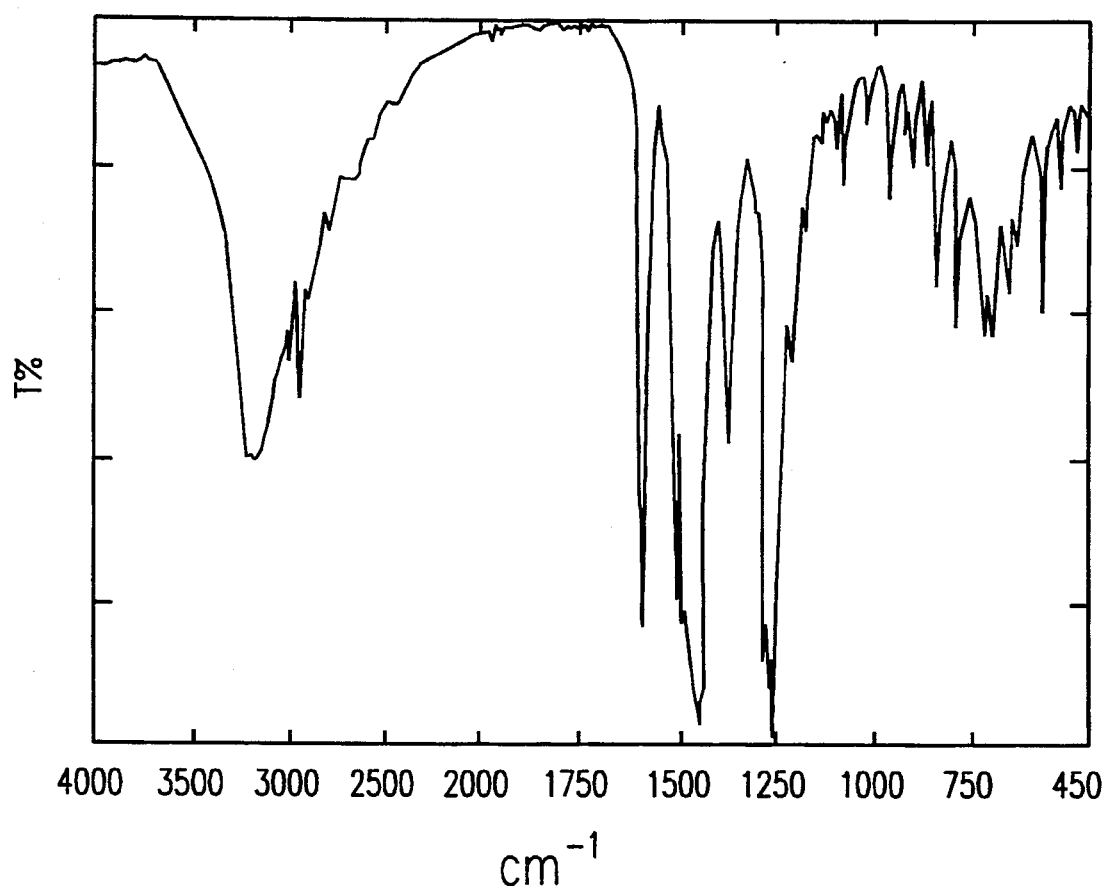
FIG. 24 is an infrared spectrum of the sample A-29.
Figure 25:
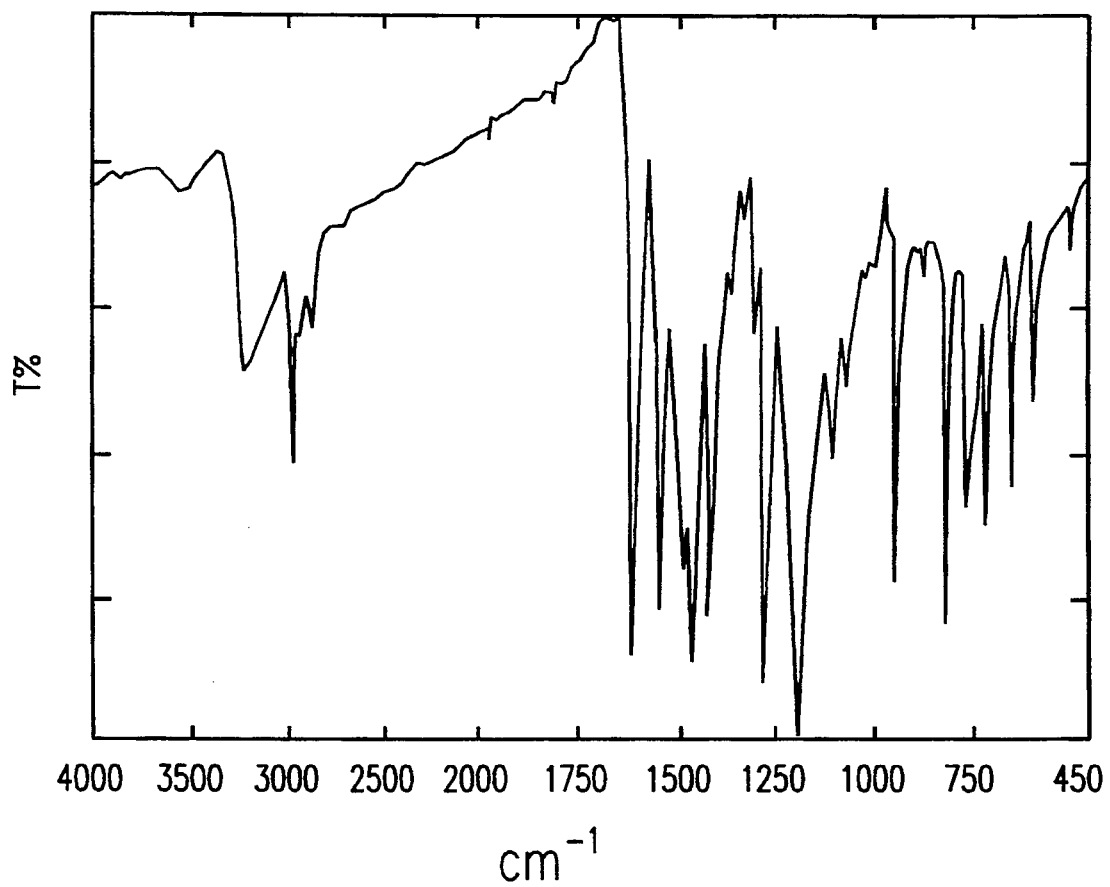
FIG. 25 is an infrared spectrum of the guest compound, hinokithiol.
Figure 26:
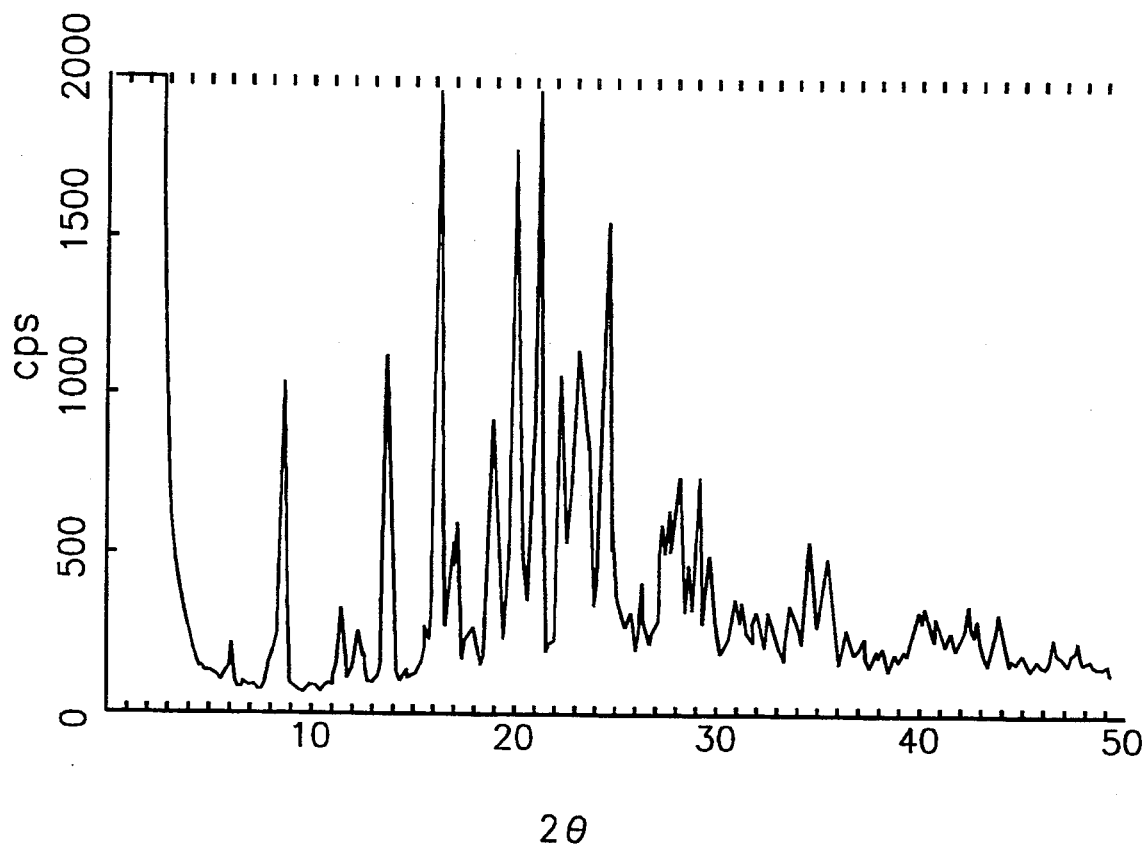
FIG. 26 is a X-ray diffraction diagram of the sample of A-29.
Figure 27:
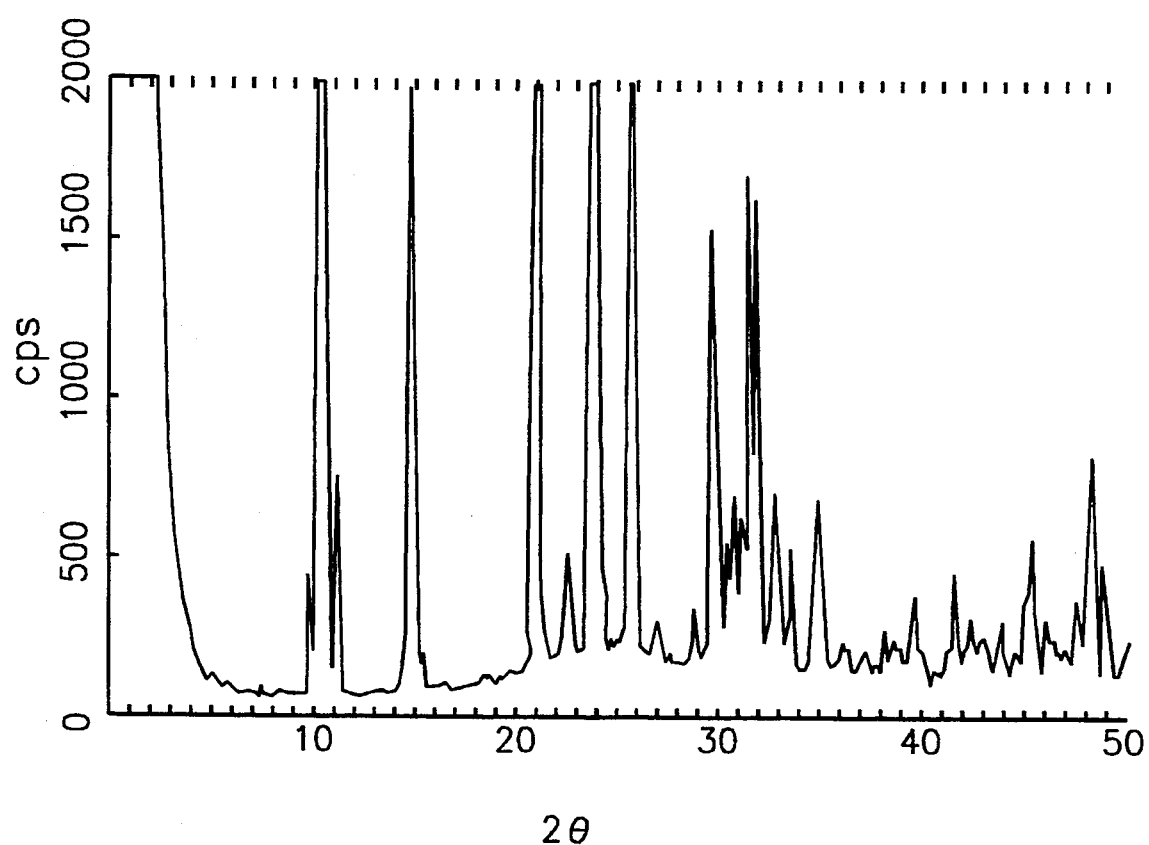
FIG. 27 is a X-ray diffraction diagram of the guest compound, hinokithiol.
Figure 28:
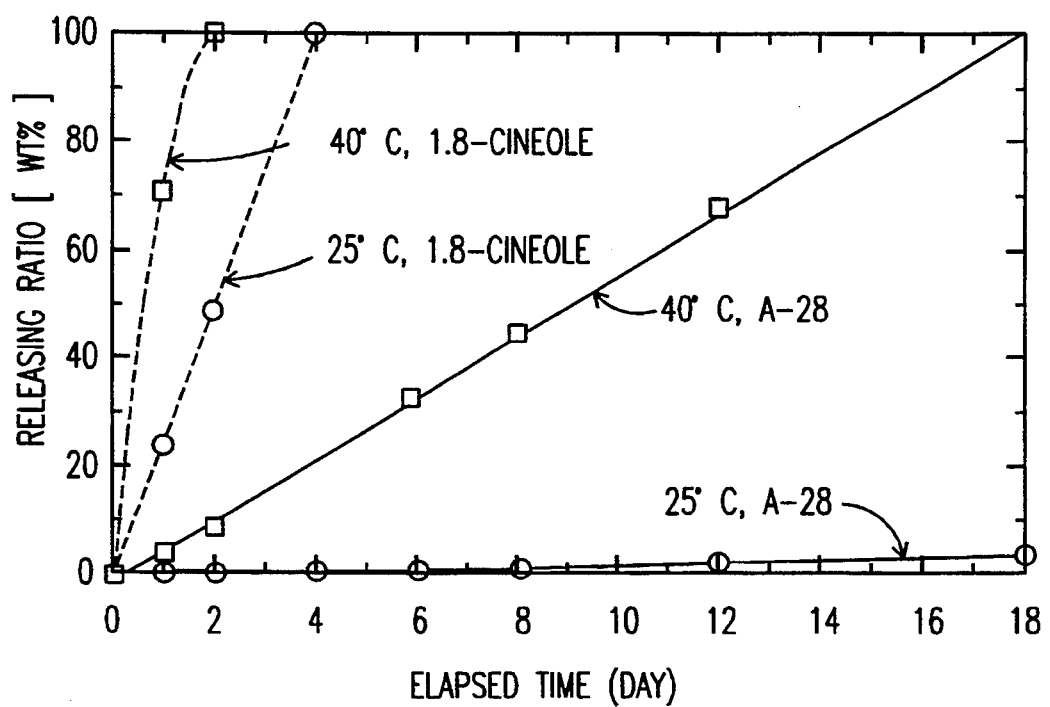
FIG. 28 shows respective release curve of A-28 and 8-cineol obtained from the release amount measured at the release tests.
Figure 29:
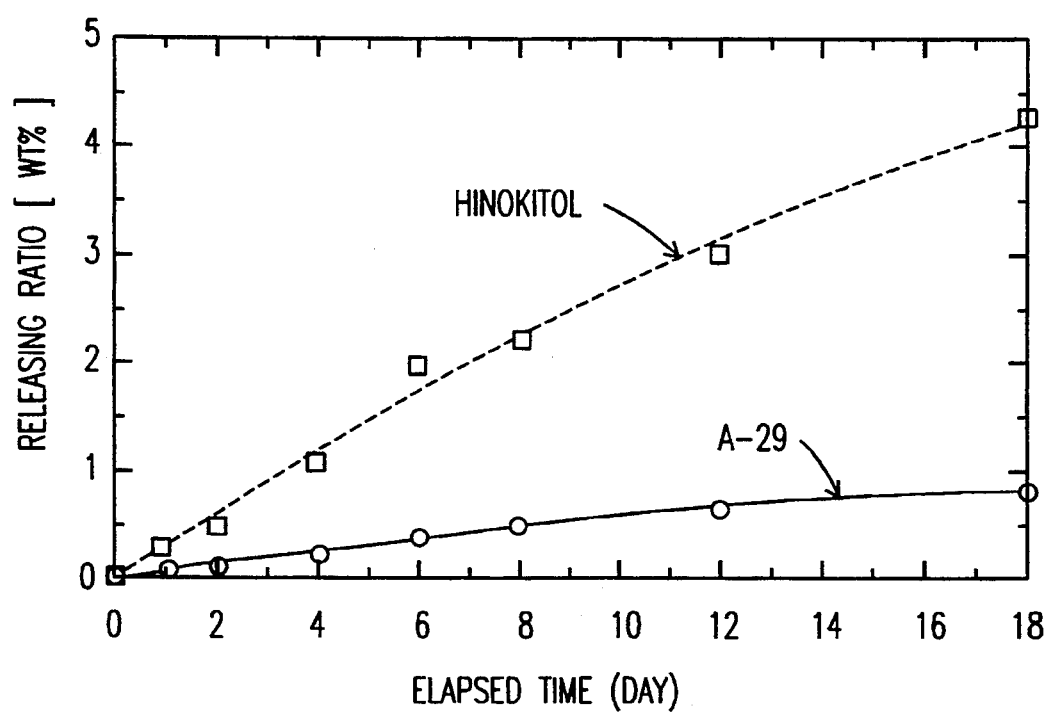
FIG. 29 shows respective release curve of each of A-29 and hinokithiol obtained from the release amount measured at the release tests.

The chemical analytical data of the representative clathrate compounds obtained in the Examples and host compounds and guest compounds those are the materials for clathrate compounds are illustrated in FIGS. 1 though 47.

EXAMPLE 1

Samples: Preparation of A-1 through A-6

As host compound, 2.51 mmol (1.0 g) of TEP-DF (Asahi Yukizai Industries) was added into 10 ml of the organic compound to be used as guest compound and the mixture was stirred with heating until TEP-DF completely dissolved in the solution. The reaction was allowed to stand for a prescribed time after the complete dissolution of TEP-DF and immediately filtered, then filtrate was allowed to stand at room temperature to deposit the crystals. After the filtration of this deposits, the samples of the compound of the present invention A-1 through A-6 were obtained by suction drying at room temperature.

EXAMPLE 2

Sample: Preparation of A-7 through A-11

2.51 mmol (1.0 g) of TEP-DF (Asahi Yukizai Industries) was added as host compound into 10 ml of the organic compound to be used as guest compound and stirred with heating until the organic compound reach to boil. The reaction was allowed under reflux for a prescribed time and the reaction mixture was cooled to room temperature to deposit the crystals. After the filtration of the crystals, the samples of the compound specified in the present invention A-7 through A-11 were obtained by suction drying at room temperature.

EXAMPLE 3

Sample: Preparation of A-12

1.0 g (2.51 mmol) of TEP-DF (Asahi Yukizai Industries) was added into 10 ml of mixed solvent (n-propanol:water=1:1 v/v) and stirred with heating until TEP-DF completely dissolved in the solvent. After the complete dissolution of TEP-DF, the solution was further stirred for a prescribed time then filtered immediately and the filtrate was allowed to stand at room temperature to deposit the crystals. The deposit was collected by filtration and dried under vacuum at room temperature, affording whitish crystalline sample A-12.

EXAMPLE 4

Sample: Preparation of A-13 and A-14

1.0 g (2.51 mmol) of TEP-DF was added into 10 ml of organic compound (ethyl acetate and 1,4-dioxane) to be the guest compound and the mixture was stirred with heating until TEP-DF Completely dissolved in the solution- After the complete dissolution of TEP-DF, the solution was further reacted for a prescribed time then filtered immediately and the filtrate was allowed to stand at room temperature to deposit the crystals. The deposit was collected by filtration and dried under vacuum at room temperature, affording the sample of the compound specified in the present invention: A-13 and A-14.

EXAMPLE 5

Sample: Preparation of A-15 and A-16

1.0 g (2.51 mmol) of TEP-DF was added into 5 ml of organic compound (diethylamine and triethylamine) as guest compound and the mixture was stirred with heating until the organic compound reached to boil, then the reaction mixture was cooled to the room temperature to deposit the crystals. The crystals were collected by filtration, then dried under vacuum at room temperature, affording the sample of the compound specified in the present invention: A-15 and A-16.

EXAMPLE 6

Sample: Preparation of A-17

1.0 g (2.51 mmol) of TEP-DF (Asahi Yukizai Industries) was added into 5 ml of methanol and the mixture was stirred with heating until TEP-DF completely dissolved in the solution. After the complete dissolution of TEP-DF, 1.2 g (4.0 mmol) of benzimidazole was gradually added and stirred for 10 minutes at 50° C. Then the mixture was filtered immediately and the filtrate was allowed to stand at room temperature to deposit the crystals. The crystals were collected by filtration, then dried under vacuum at room temperature, affording whitish crystalline sample: A-17.

EXAMPLE 7

Sample: Preparation of A-18

1.0 g (2.51 mmol) of TEP-DF (Asahi Yukizai Industries) was added into 5 ml of i-propanol. After the complete dissolution of TEP-DF, 1.2 g (4.0 mmol) of benzimidazole was gradually added into the solution, then the mixture was stirred for 10 minutes at 80° C. The reaction mixture was immediately filtered, and the filtrate was allowed to stand at room temperature to deposit the crystals. The crystals were collected by filtration, then dried under vacuum at room temperature, affording whitish crystalline sample: A-18.

The samples obtained: The manufacturing condition for A-1 through A-18, guest/host mol ratio in the clathrate compound obtained, and the releasing temperature of the guest compounds were summarized in Table 1.

EXAMPLE 8

Sample: Preparation of A-19 and A-20

1.0 g (2.51 mmol) of TEP-DF (Asahi Yukizai Industries) was added into 5 ml of methanol and the mixture was stirred with heating until TEP-DF completely dissolved in the solution. Then 5 ml of pyridine (or pyrrole) which is a corresponding guest compound was gradually fed dropwise into the solution and stirred for 10 minutes at 60° C. Then the reaction mixture was immediately filtered and the filtrate was allowed to stand at room temperature to deposit the crystals. The crystals were collected by filtration and dried under vacuum at room temperature, affording the sample in whitish powder of the compound specified in the present invention: A-19 and A-20. The yield was 84% for A-19 and 70% for A-20 in conversion to the host compound.

EXAMPLE 9

Sample: Preparation of A-21

1.0 g (2.51 mmol) of TEP-DF was added into 5 ml of isopropanol and the mixture was stirred with heating until TEP-DF completely dissolved in the solution. Then 5 ml of pyrrole was gradually fed dropwise into the solution and stirred for 30 minutes at 80° C. Then the reaction mixture was immediately filtered and the filtrate was allowed to stand at room temperature to deposit the crystals. The crystals were collected by filtration and dried under vacuum at room temperature, affording the sample in whitish powder of the compound specified in the present invention: A-21. The yield was 68% when calculated with host compound.

EXAMPLE 10

Sample: Preparation of A-22 through A-25

1.0 g (2.51 mmol) of TEP-DF was added into 5 ml of methanol and the mixture was stirred with heating until TEP-DF completely dissolved in the solution. Then 10.04 ml of corresponding guest compound (pyrazine, pyrazole, imidazole, 1,2,4-triazole) was added into the solution and stirred for 20 minutes at 60°. Then the reaction mixture was immediately filtered and the filtrate was allowed to stand at room temperature to precipitate the crystals. The crystals were collected by filtration and dried under vacuum at room temperature, affording the sample in whitish powder of the compound specified in the present invention: A-22 through A-25. The yields were 82% for A-22, 85% for A-23, 73% for A-24 and 95% for A-25 respectively in conversion to the host compound.

EXAMPLE 11

Sample: Preparation of A-26 and A-27

1.0 g (2.51 mmol) of TEP-DF was added into 5 ml of guest compound, pyridine (or pyrrole) and the gel suspension was obtained after stirring at room temperature. After separating the suspended materials in the suspension by filtration, the filtrate was dried under vacuum at room temperature, affording the sample in whitish powder of tile compound specified in the present invention: A-26 and A-27. The yields were 100% for A-26 and 100% for A-27 in conversion to the host compound. The manufacturing condition of respective sample, guest/host mol ratio of the clathrate compounds obtained and the releasing temperature of the guest compounds were summarized in Table 2.

EXAMPLE 12

Sample: Preparation of A-28

1.0 g (2.51 mmol) of TEP-DF (Asahi Yukizai Industries) was added into 5 ml of methanol and the mixture was stirred with heating until TEP-DF completely dissolved in the solution. Then 1.55 g (10.04 mmol) of 1,8-cineole was gradually fed dropwise into the solution and stirred for 10 minutes at 60° C. to react the solution. Then the reactant solution was immediately filtered and the filtrate was allowed to stand at room temperature to deposit the crystals. The crystals were collected by filtration and dried under vacuum at room temperature, affording the sample in whitish powder A-28.

EXAMPLE 13

Sample: Preparation of A-29

1.0 g (2.51 mmol) of TEP-DF was added into 5 ml of methanol and the mixture was stirred with heating until TEP-DF completely dissolved in the solution. Then 1.65 g (10.04 mmol) of hinokithiol was gradually fed dropwise into the solution and stirred for 10 minutes at 60° C. Then the reaction mixture was immediately filtered and the filtrate was allowed to stand at room temperature to deposit the crystals. The crystals were collected by filtration and dried under vacuum at room temperature, affording the sample in whitish powder A-29.

EXAMPLE 14

Sample: Preparation of A-30

1.0 g (2.51 mmol) of TEP-DF was added into 5 ml of benzene and dispersed in suspension by stirring. Then 1.57 g (10.04 mmol) of 1-menthol was added into the suspension, stirred for 30 minutes at 40° C. and then cooled to room temperature. The suspension was separated by filtration and the filtrate was dried under vacuum at room temperature, affording the sample in whitish powder A-30.

EXAMPLE 15

Sample: Preparation of A-31

1.0 g (2.51 mmol) of TEP-DF was added into 1.55 g (10.04 mmol) of α-terpineol and the mixture was reacted at 60° C. under stirring, then a solid substance was obtained. After grinding this solid substance, the resulting powder was dried under vacuum, affording the sample in whitish powder A-31.

The manufacturing condition of respective samples obtained in the above, guest/host mol ratio in the clathrate compounds obtained and the releasing temperature of the guest compounds were summarized in Table 3.

EXAMPLE 16

The obtained samples, A-28 and A-29 and comparative samples, 1,8-cineole (R-1) and hinokithiol (R-2) equivalent containing 0.6 g of guest compound are taken into Petri dish respectively and set in the desiccators maintained at the temperature of 25° and 40° C. The dried air was introduced into the desiccator at rate of 250 ml/min and the decrease of the weight was measured periodically. The results were shown in Table 4.

Figure 30:
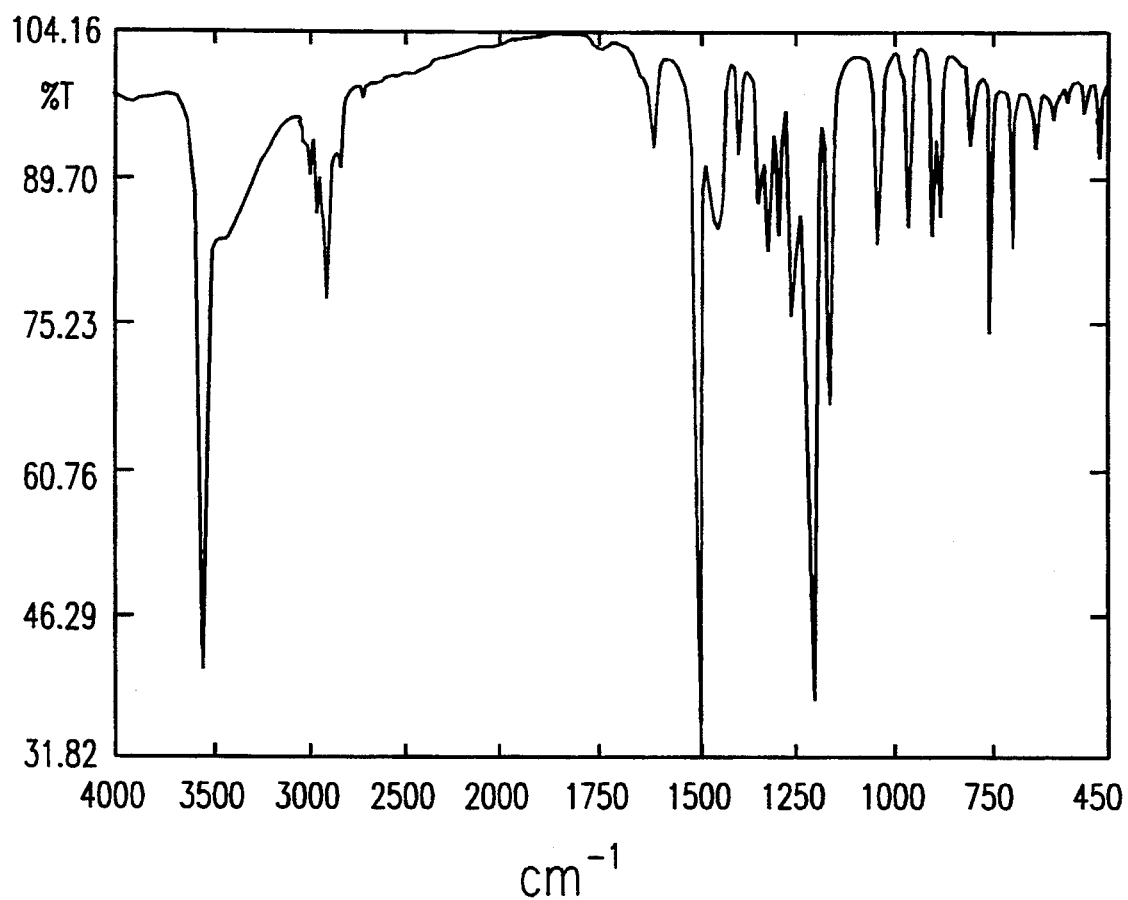
FIG. 30 is an infrared spectrum (KBr) of 1,1,2,2-tetrakis(3,5-dimethyl-4-hydroxyphenyl)ethane obtained in the synthetic Example 1-1.
Figure 31:
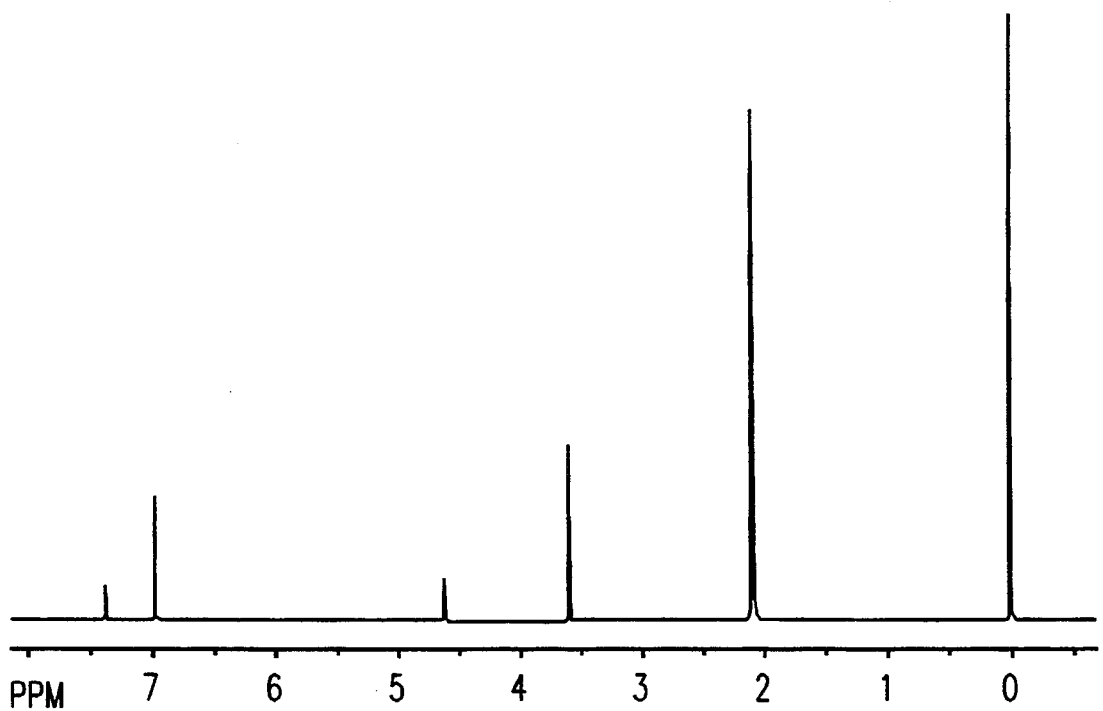
FIG. 31 is a $^1$H-NMR spectrum ($d^6$-Acetone, TMS) of 1,1,2,2-tetrakis(3,5-dimethyl-4-hydroxyphenyl)ethane obtained in the synthetic Example 1-1.

(1) Synthesis of host compound (Synthetic Example 1)
(1-1) Synthesis of 1,1,2,2-tetrakis(3,5-dimethyl-4-hydroxyphenyl)ethane:

14.5 g of 40% aqueous solution of glyoxal and 54.9 g of 2,6-xylol were applied into 300 ml flask, then 100 ml of the mixture of concentrated sulfuric acid and phosphoric acid (ratio 3:1, v/v) was fed dropwise with stirring over 2 hours at the titration temperature of 0°-2° C. After titration, the mixture was stirred for 4 hours at 0° C. The reaction mixture was poured into 600 ml of ice-water, then the temperature of the solution was raised to 70° C. to collect the deposited solid by filtration. The solid was recrystallized from dioxane, then dried under vacuum at 100° C., affording 15.0 g of whitish powder. The yield was 29.4%. The powder was identified as 1,1,2,2-tetrakis(3,5-dimethyl-4-hydroxyphenyl)ethane by means of both infrared spectrum and NMR spectrum. The chart of each measurement was shown in FIG. 30 and FIG. 31.

Figure 32:
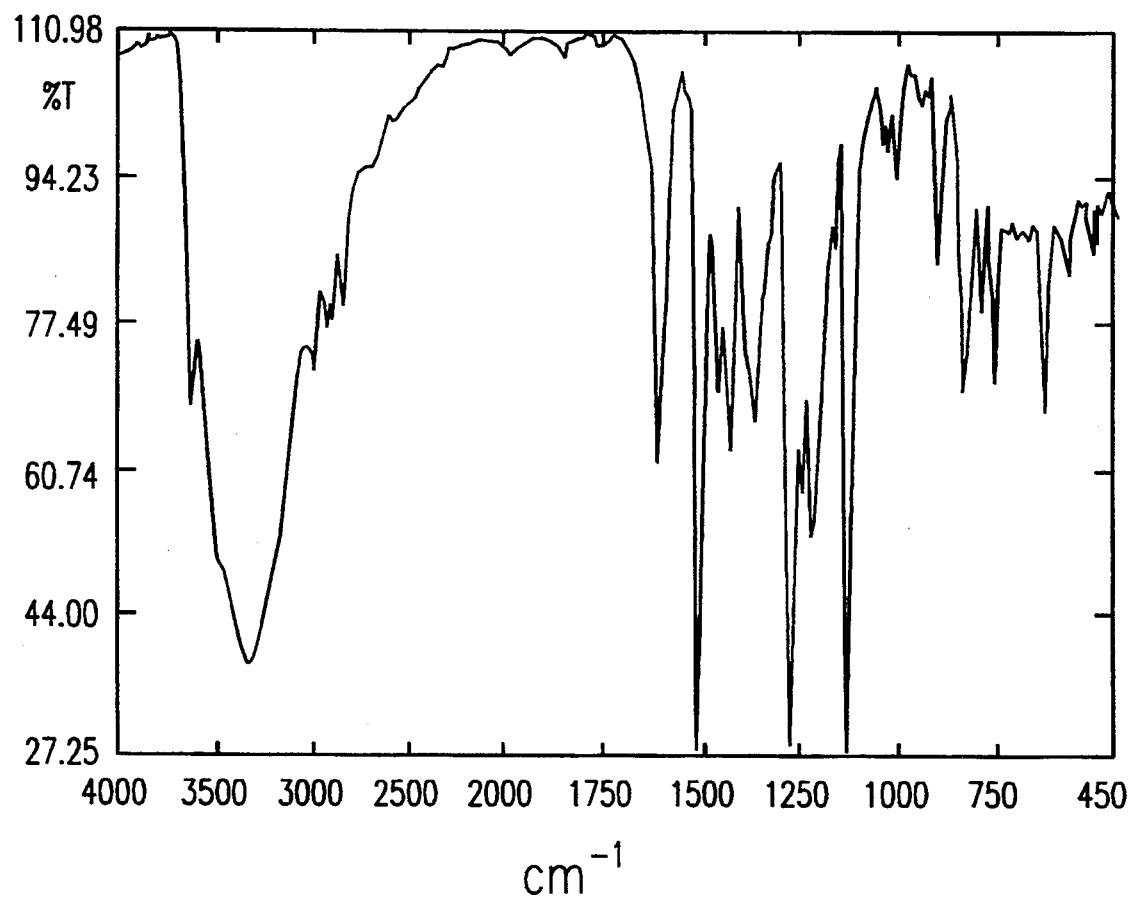
FIG. 32 is an infrared spectrum (KBr) of 1,1,2,2-tetrakis(3-methyl-4-hydroxyphenyl)ethane obtained in the synthetic Example 1-2.
Figure 33:
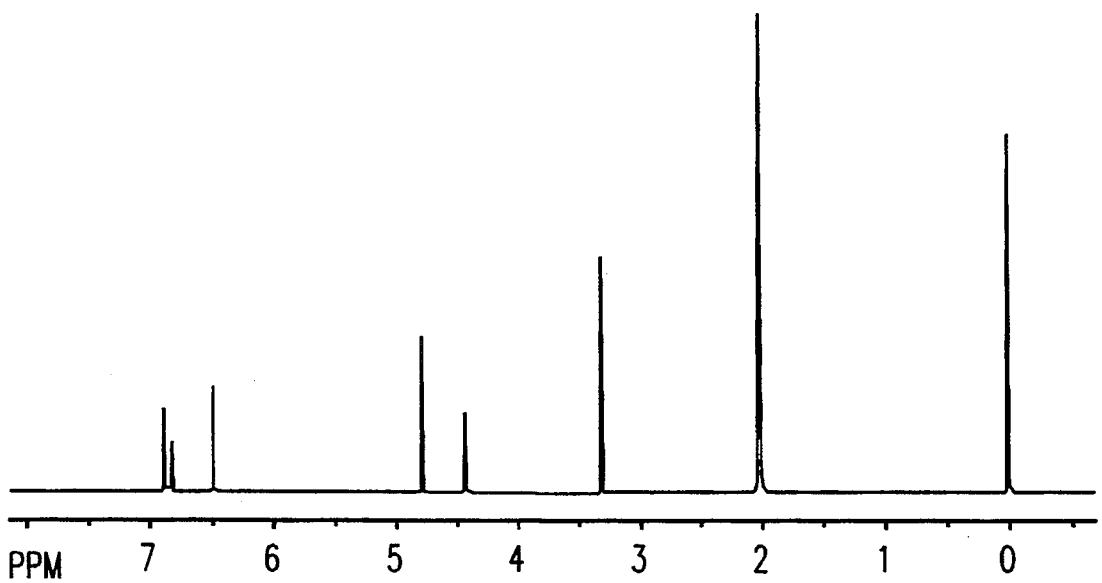
FIG. 33 is a $^1$H-NMR spectrum (d-MeOH, TMS) of 1,1,2,2-tetrakis(3-methyl-4-hydroxyphenyl)ethane obtained in the synthetic Example 1-2.

(1-2) Synthesis of 1,1,2,2-tetrakis(3-methyl-4-hydroxyphenyl)ethane:

14.5 g of 40% aqueous solution of glyoxal and 51.8 g of o-cresol were applied into 300 ml flask, then 100 ml of the mixture of concentrated sulfuric acid and phosphoric acid (volumetric ratio 3:1) was fed dropwise with stirring over 2 hours at the titration temperature of 0°-2 ° C. The mixture was stirred for 4 hours at 0° C. After the end of the reaction, the reaction mixture was poured into 600 ml of ice-water, then the temperature of the solution was raised to 70° C. to collect the deposited solid by filtration. The solid was recrystallized form dioxane, then dried under vacuum at 100° C., affording 17.0 g of whitish powder. The yield was 37.4%. The powder was identified as 1,1,2,2-tetrakis(3-methyl-4-hydroxyphenyl)ethane by means of both infrared spectrum and NMR spectrum. The chart of each measurement was shown in FIG. 32 and FIG. 33.

Figure 34:
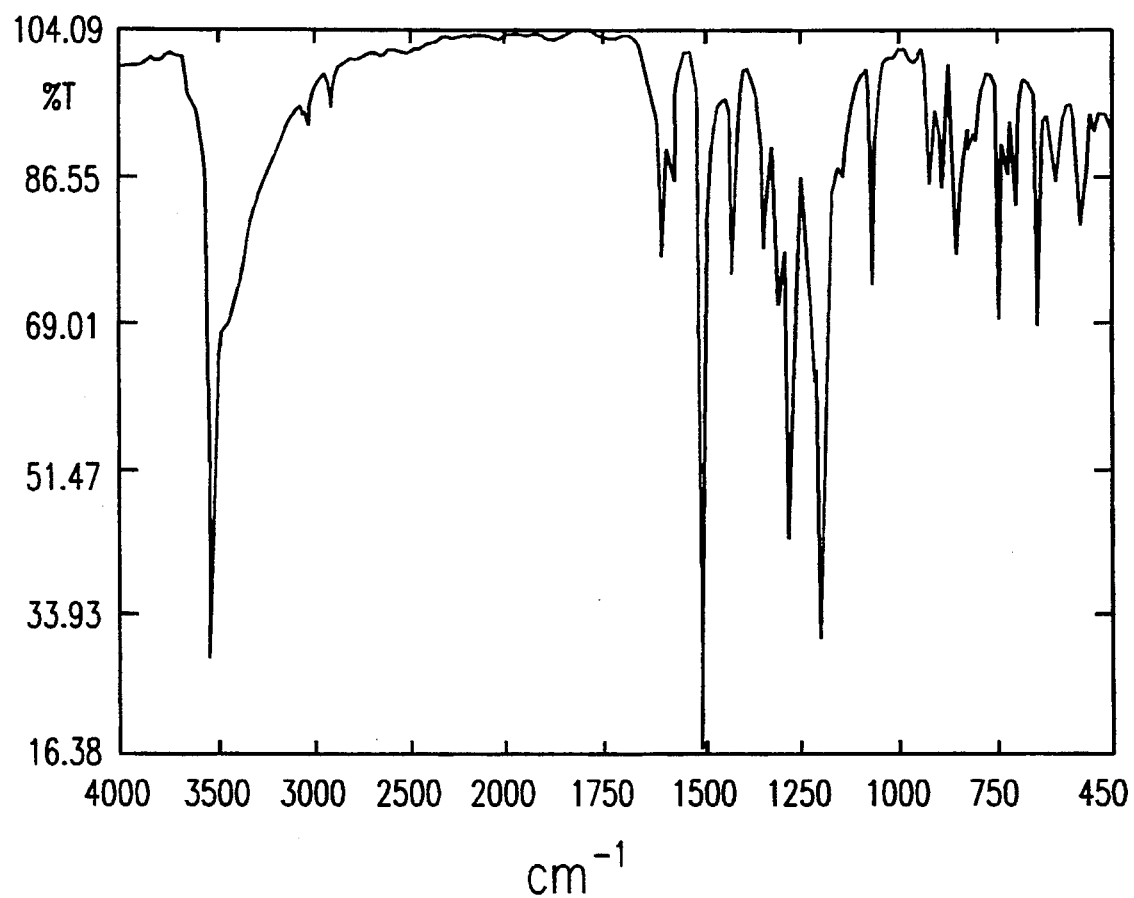
FIG. 34 is an infrared spectrum (KBr) of 1,1,2,2-tetrakis(3-chloro-4-hydroxyphenyl)ethane obtained in the synthetic Example 1-3.
Figure 35:
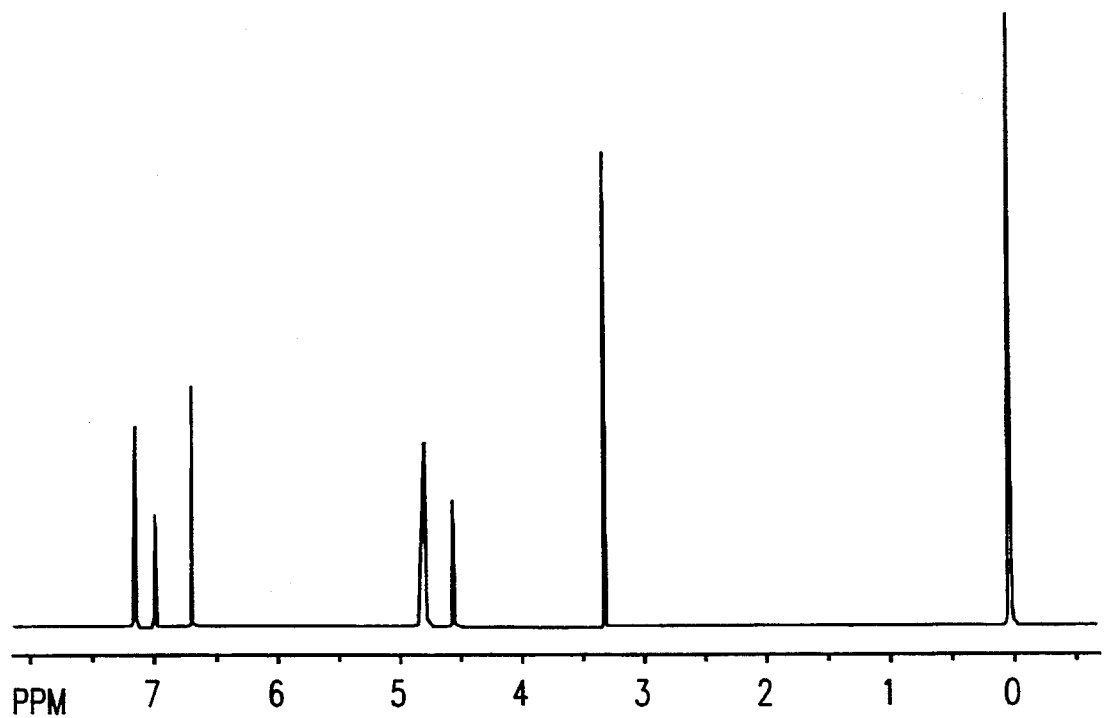
FIG. 35 is a $^1$H-NMR spectrum (d-MeOH, TMS) of 1,1,2,2-tetrakis(3-chloro-4-hydroxyphenyl)ethane obtained in the synthetic Example 1-3.

(1-3) Synthesis of 1,1,2,2-tetrakis(3-chloro-4-hydroxyphenyl)ethane:

14.5 g of 40% aqueous solution of glyoxal and 56.6 g of 2-chlorophenol were applied into 300 ml flask, then 100 ml of the mixture of concentrated sulfuric acid and phosphoric acid (volumetric ratio 3:1) was fed dropwise with stirring over 2 hours at the titration temperature of 0°-2° C. Following that, the mixture was stirred for 4 hours at 0° C. The reaction mixture was poured into 600 ml of ice-water, then it was extracted three times with 100 ml of ether after the addition of NaCl. The ether layer was added with sodium sulfate anhydride and dehydrated, then ether and unreacted 2-chlorophenol were removed by distillation under reduced pressure. After the distillation, the residues were recrystallized from dioxane, then dried under vacuum at 100° C., affording 7.5 g of whitish powder. The yield was 14.0%. The powder was identified as 1,1,2,2-tetrakis(3-chloro-4-hydroxyphenyl) ethane by means of both infrared spectrum and NMR spectrum. The chart of each measurement was shown in FIG. 34 and FIG. 35.

Figure 36:
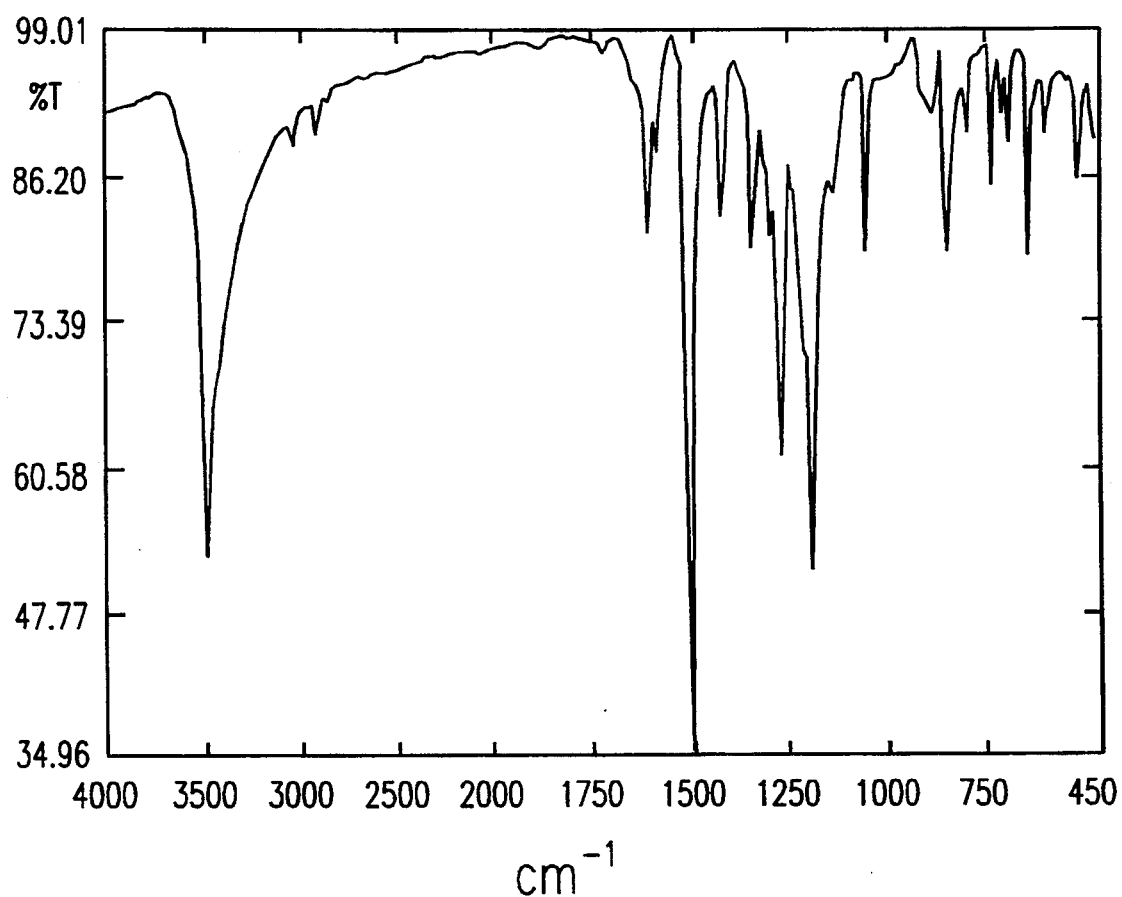
FIG. 36 is an infrared spectrum (KBr) of 1,1,2,2-tetrakis(3-bromo-4-hydroxyphenyl)ethane obtained in the synthetic Example 1-4.
Figure 37:
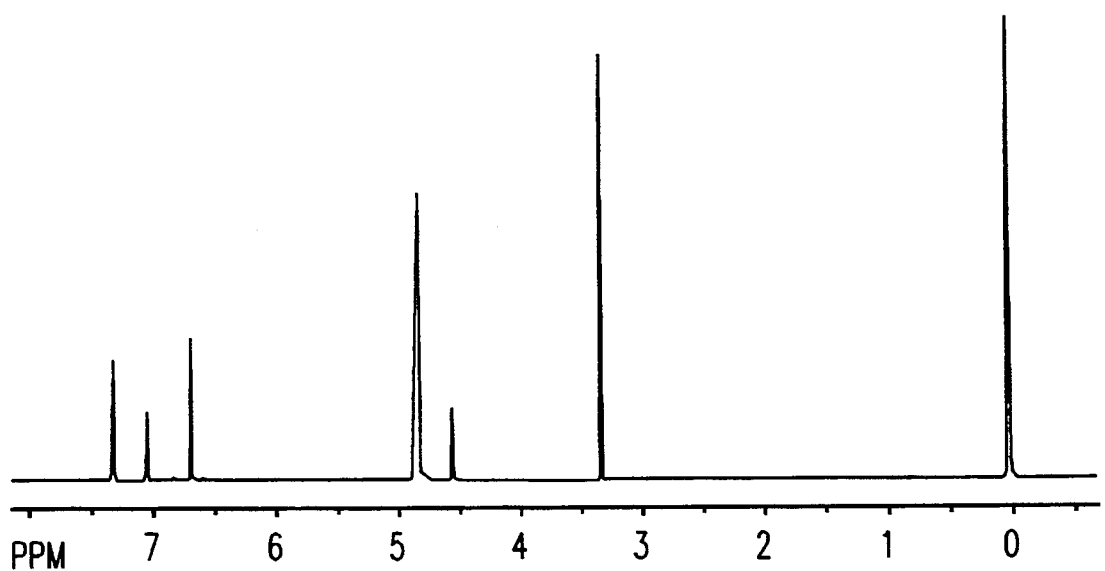
FIG. 37 is a $^1$H-NMR spectrum (d-MeOH, TMS) of 1,1,2,2-tetrakis(3-bromo-4-hydroxyphenyl)ethane obtained in the synthetic Example 1-4.

(1-4) Synthesis of 1,1,2,2-tetrakis(3-bromo-4-hydroxyphenyl)ethane:

10.9 g of 40% aqueous solution of glyoxal and 57.1 g of 2-bromophenol were applied into 300 ml flask, then 70 ml of the mixture of concentrated sulfuric acid and phosphoric acid (volumetric ratio 3:1) was fed dropwise with stirring over 1.5 hours at the titration temperature of 0°-2° C. Following that, the mixture was stirred for 5 hours at 0° C. The reaction mixture was poured into 500 ml of ice-water, then it was extracted three times with 100 ml of ether after the addition of NaCl. The ether layer was added with sodium sulfate anhydride and dehydrated, then ether and unreacted 2-bromophenol were removed by distillation under reduced pressure. After the distillation, the residues were recrystallized from dioxane, then dried under vacuum at 100° C., affording 3.1 g of whitish powder. The yield was 5.8%. The powder was identified as 1,1,2,2-tetrakis(3- bromo-4-hydroxyphenyl) ethane by means of both infrared spectrum and NMR spectrum. The chart of each measurement was shown in FIG. 36 and FIG. 37.

Figure 38:
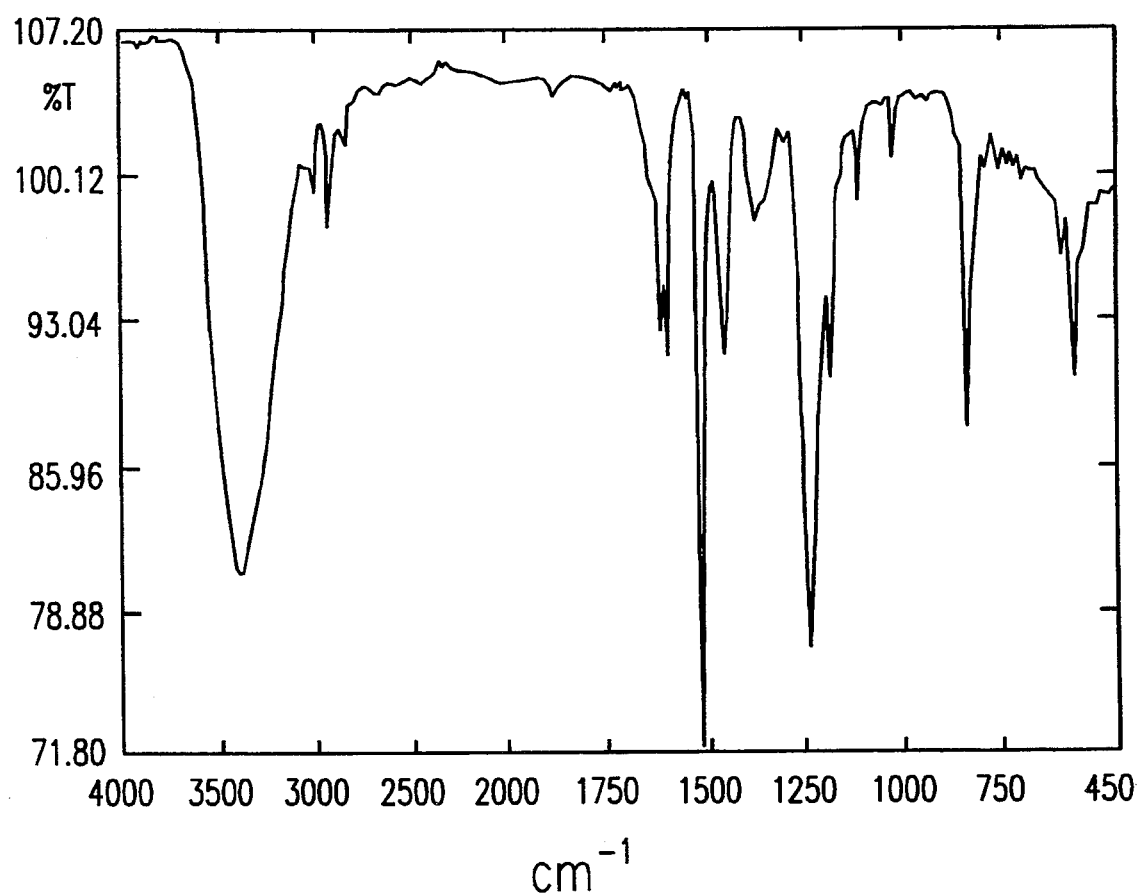
FIG. 38 is an infrared spectrum (KBr) of 1,1,4,4-tetrakis(4-hydroxyphenyl)butane obtained in the synthetic Example 1-6.
Figure 39:
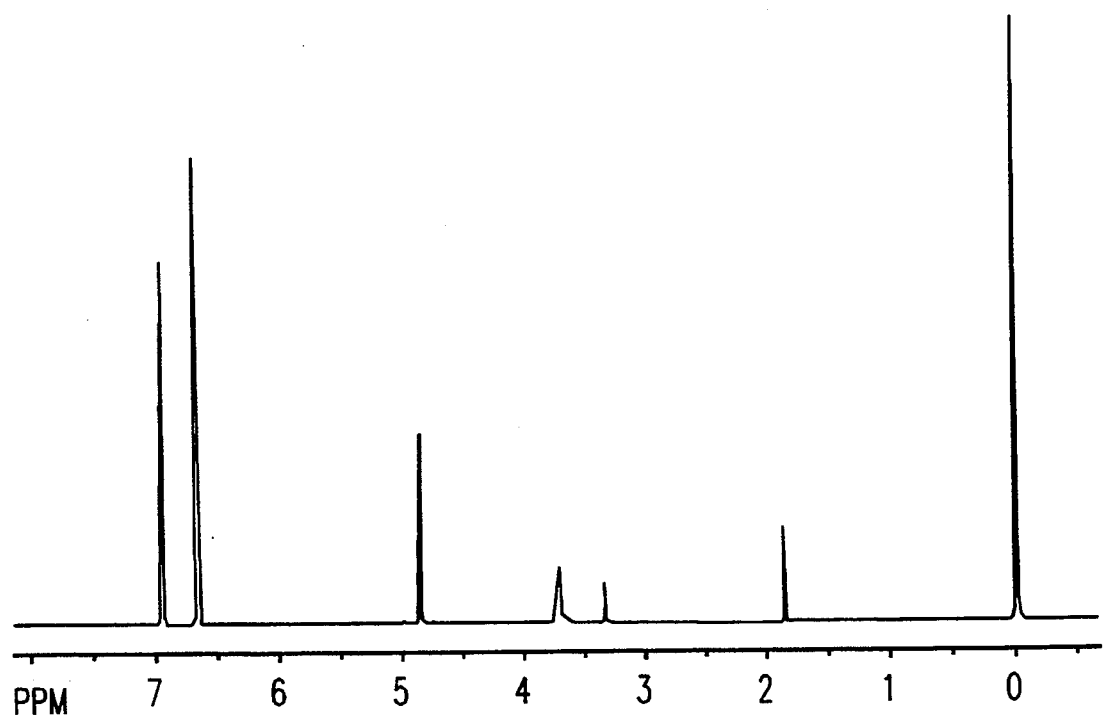
FIG. 39 is a $^1$H-NMR spectrum (d-MeOH, TMS) of 1,1,4,4-tetrakis(4-hydroxyphenyl)ethane obtained in the synthetic Example 1-6.

(1-5) Synthesis of 1,1,5,5-tetrakis(4-hydroxyphenyl) pentane:

20.0 g of 50% aqueous solution of glutaric aldehydes and 45.1 g of phenol were applied into 300 ml flask, then 200 ml of the mixture of concentrated sulfuric acid and phosphoric acid (volumetric ratio 3:1) was fed dropwise with stirring over 2 hours at the titration temperature of 0°-2° C. Following that, the mixture was stirred for 5 hours at 0° C. The reaction mixture was poured into 600 ml of ice-water, then the temperature of the solution was raised to 70° C. to collect the deposited solid by filtration. The solid was recrystallized from dioxane, then dried under vacuum at 100° C., affording 11.9 g of whitish powder. The yield was 27.9%. The powder was identified as 1,1,4,4-tetrakis(4-hydroxyphenyl)butane by means of both infrared spectrum and NMR spectrum. The chart of each measurement was shown in FIG. 38 and FIG. 39.

Figure 40:
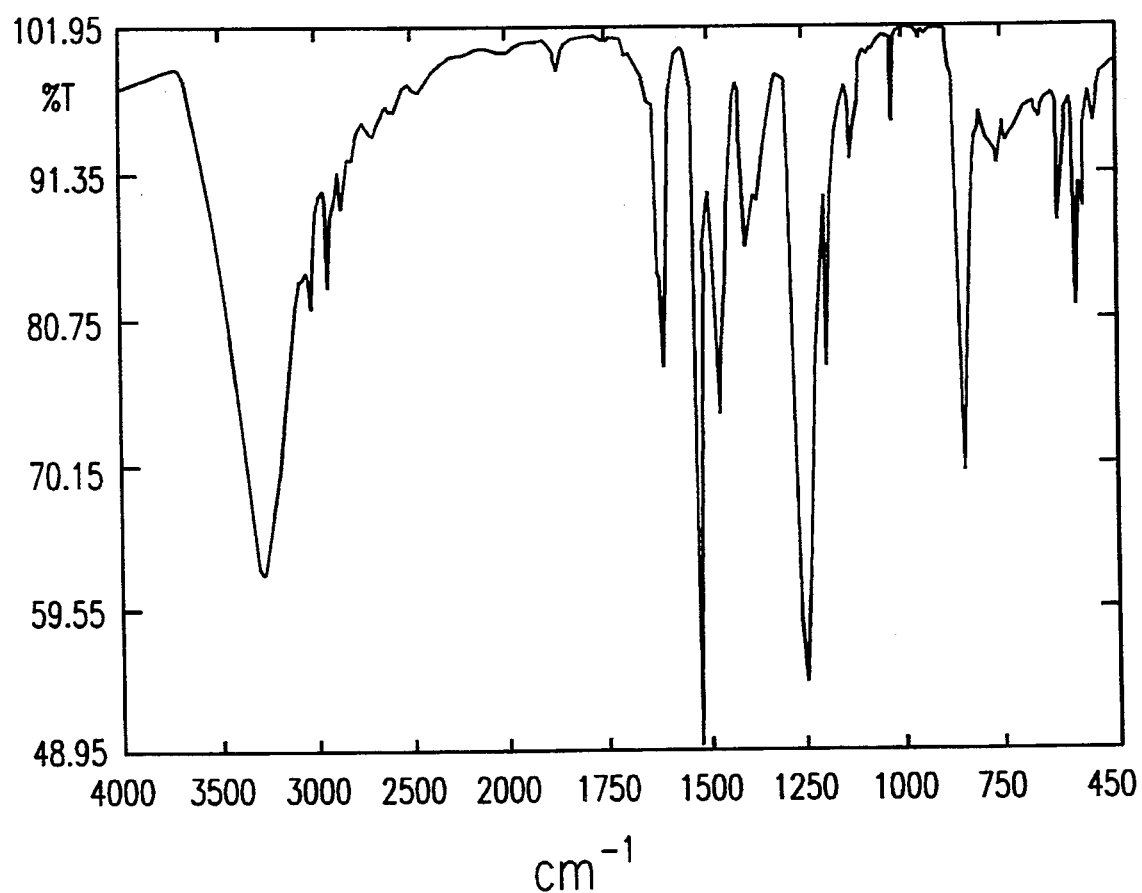
FIG. 40 is an infrared spectrum (KBr) of 1,1,5,5-tetrakis(4-hydroxyphenyl)pentane obtained in the synthetic Example 1-5.
Figure 41:
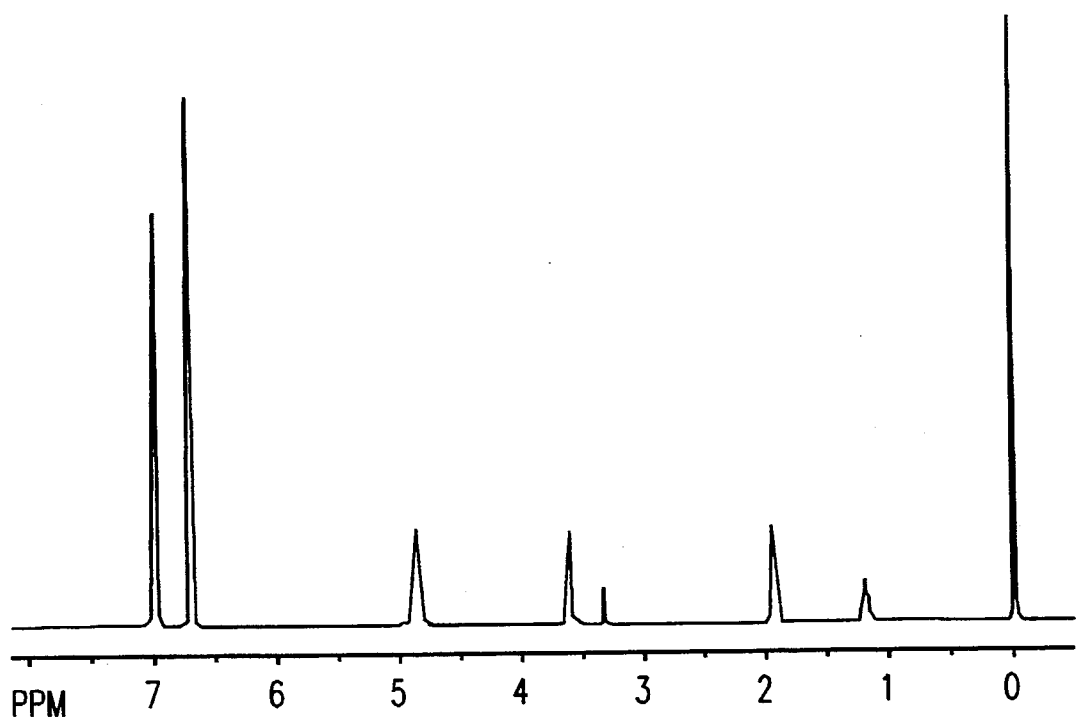
FIG. 41 is a $^1$H-NMR spectrum (d-MeOH, TMS) of 1,1,5,5-tetrakis(4-hydroxyphenyl)pentane obtained in the synthetic Example 1-5.
Figure 42:
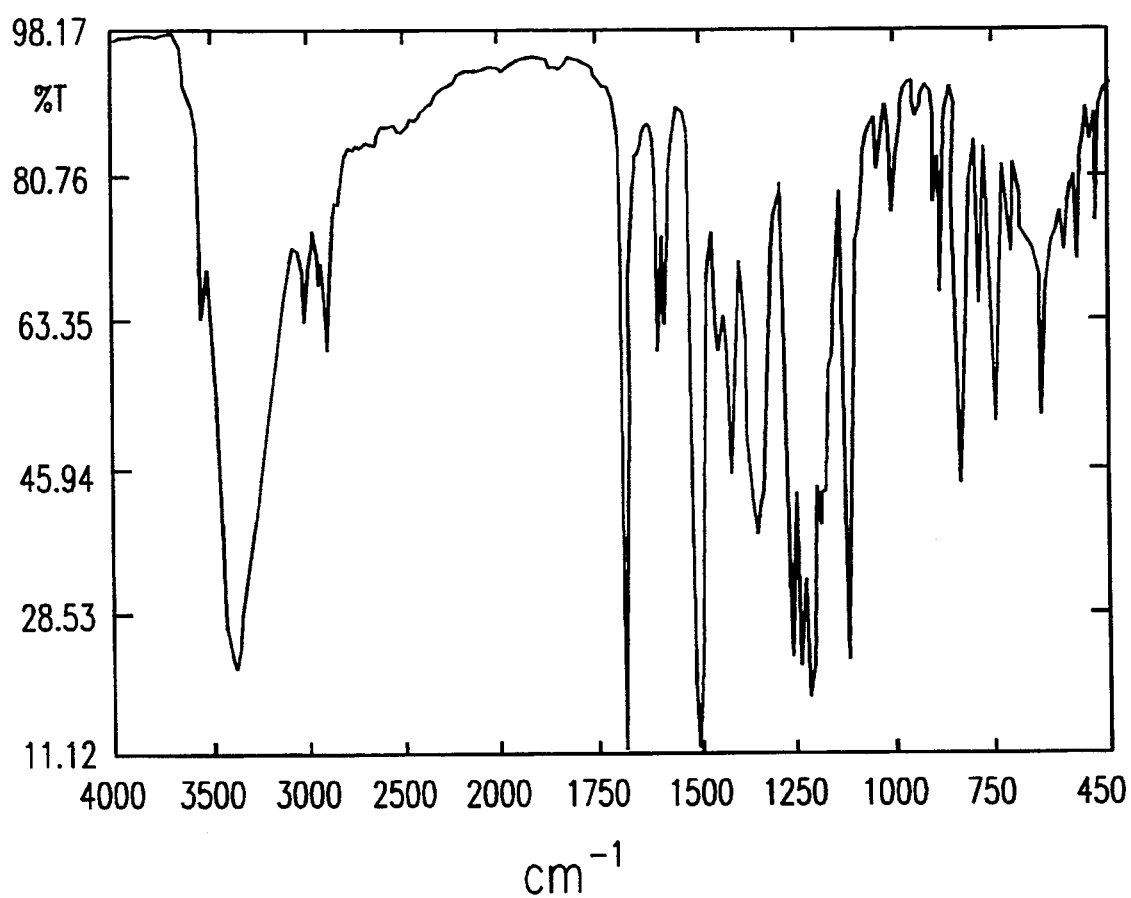
FIG. 42 is an infrared spectrum (KBr) of the clathrate compound (A-39) wherein the host compound is 1,1,2,2-tetrakis(3-methyl-4-hydroxyphenyl) ethane obtained in synthetic Example 1-2 and the guest compound is acetone.
Figure 43:
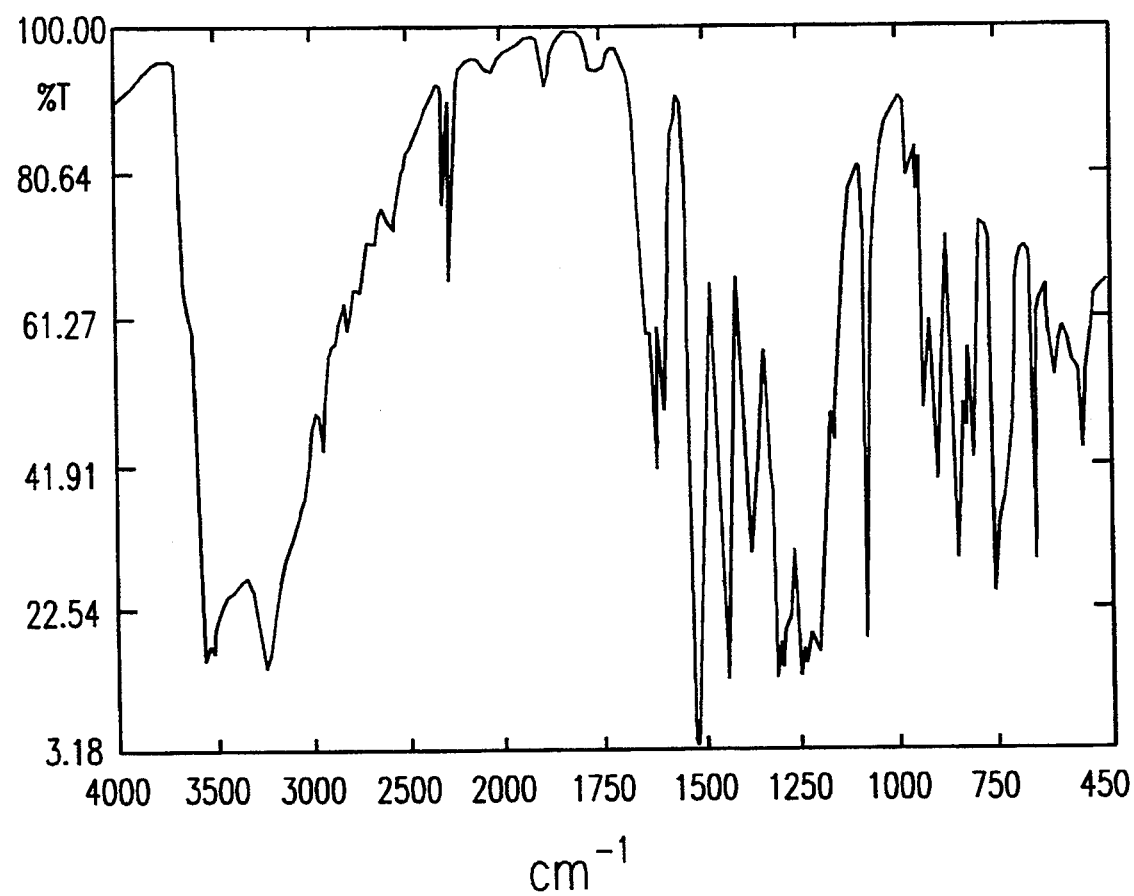
FIG. 43 is an infrared spectrum (KBr) of the clathrate compound (A-47) wherein the host compound is 1,1,2,2-tetrakis(3-chloro-4-hydroxyphenyl) ethane obtained in synthetic Example 1-3 and the guest compound is acetonitrile.
Figure 44:
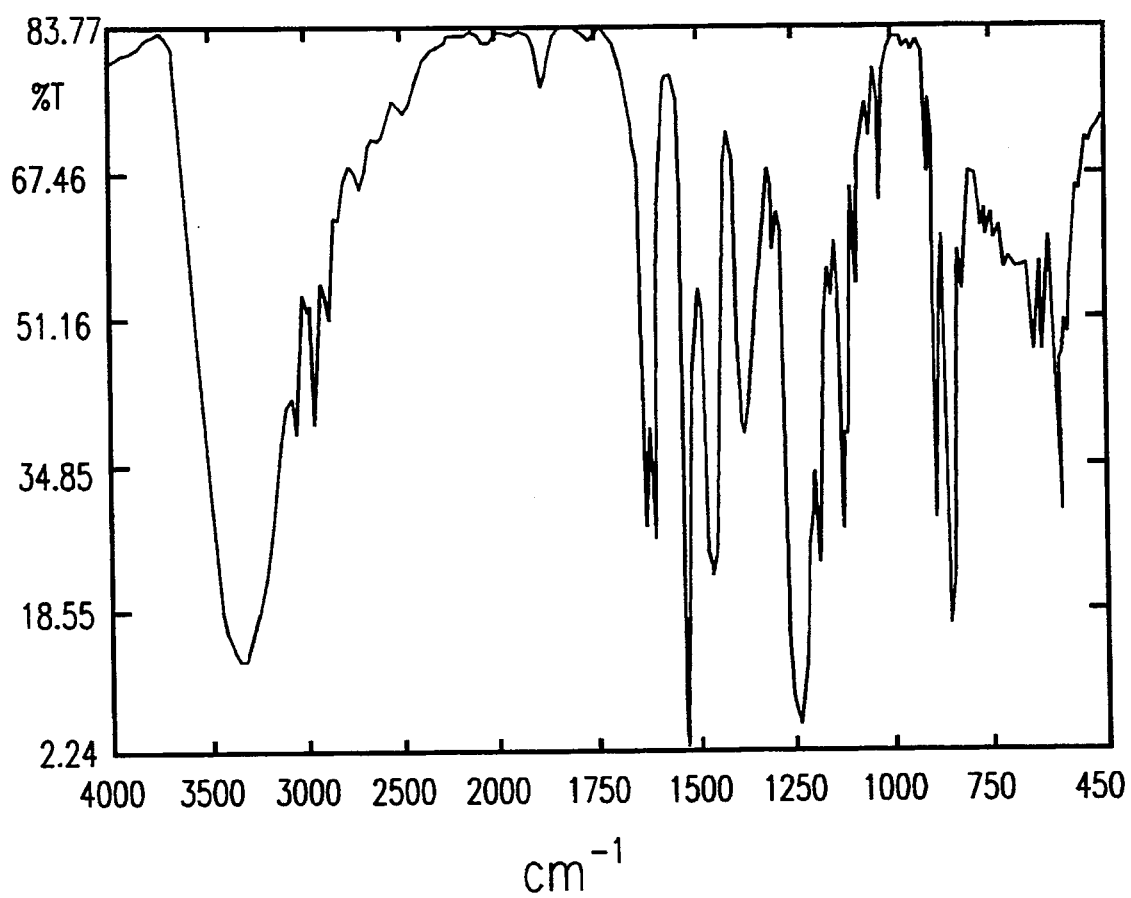
FIG. 44 is an infrared spectrum (KBr) of the clathrate compound (A-54) wherein the host compound is 1,1,5,5-tetrakis(4-hydroxyphenyl)pentane obtained in synthetic Example 1-5 and the guest compound is 1,4-dioxane.
Figure 45:
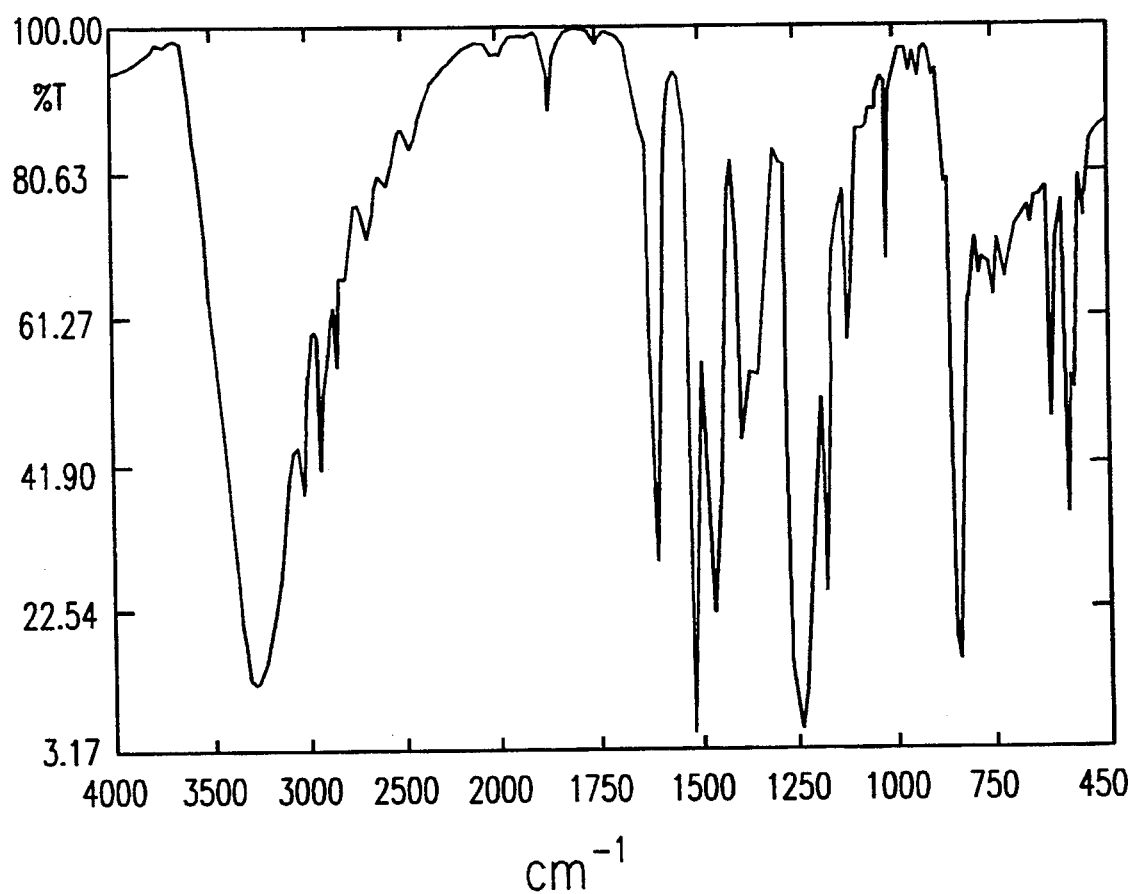
FIG. 45 is an infrared spectrum (KBr) of the clathrate compound (A-56) wherein the host compound is 1,1,4,4-tetrakis(4-hydroxyphenyl)butane obtained in synthetic Example 1-6 and the guest compound is 1,4-dioxane.
Figure 46:
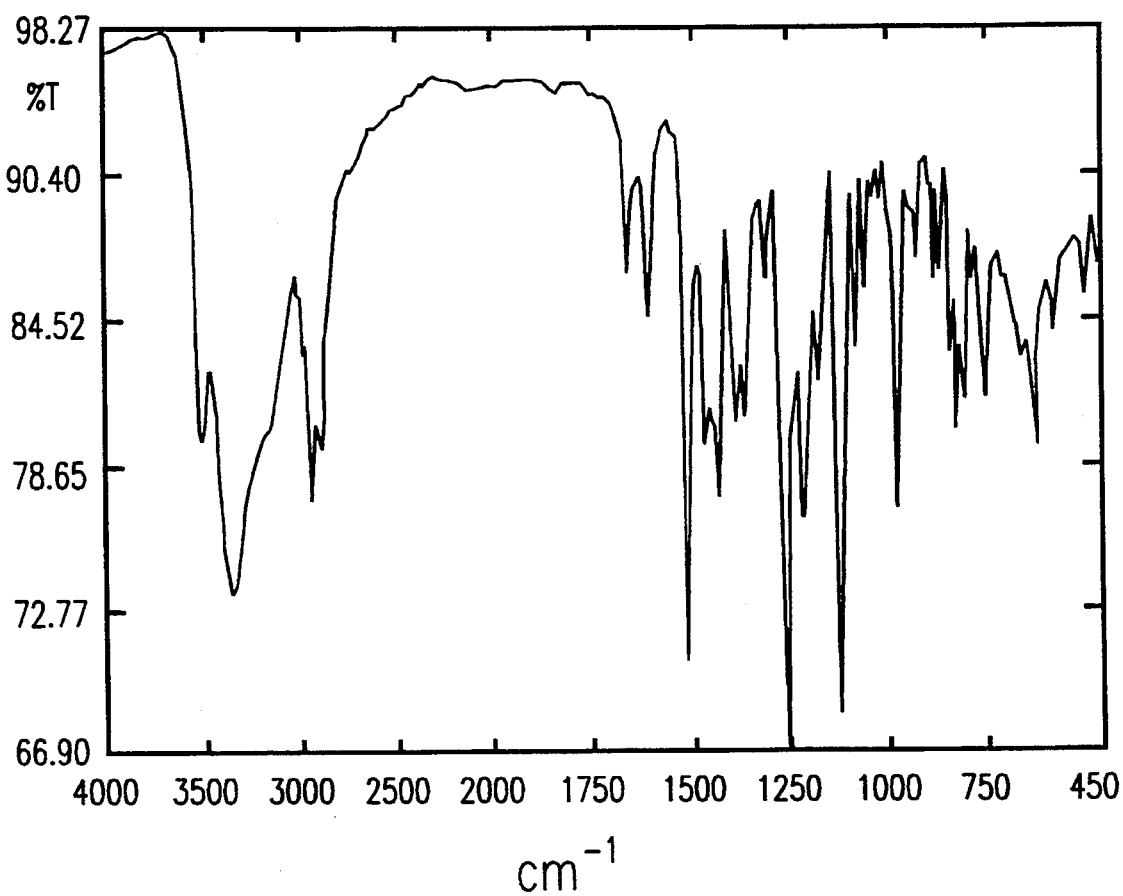
FIG. 46 is an infrared spectrum (KBr) of the clathrate compound (A-57) wherein the host compound is 1,1,2,2-tetrakis(3-methyl-4-hydroxyphenyl) ethane obtained in synthetic Example 1-1 and the guest compound is cineol.
Figure 47:
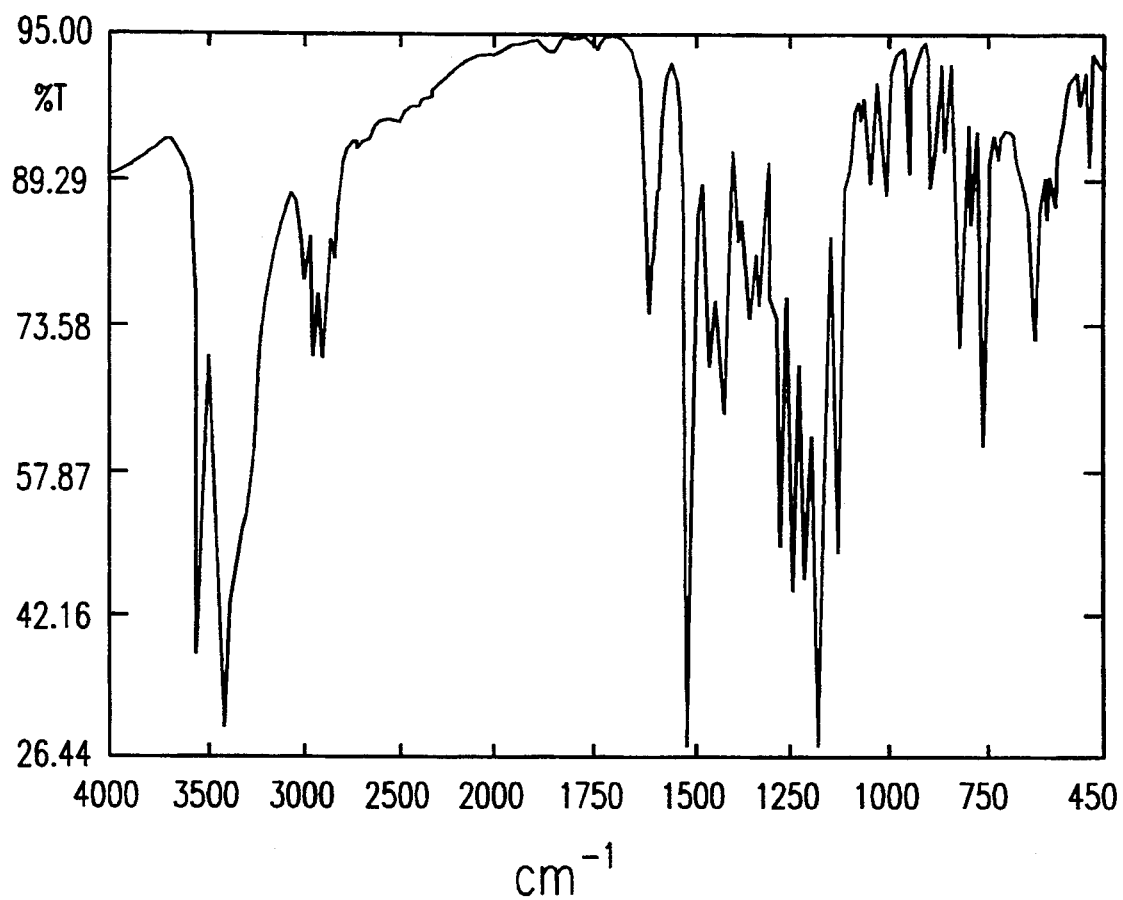
FIG. 47 is an infrared spectrum (KBr) of the clathrate compound (A-59) wherein the host compound is 1,1,2,2-tetrakis(3-methyl-4-hydroxyphenyl) ethane obtained in synthetic Example 1-2 and the guest compound is thymol.

(1-6) Synthesis of 1,1,4,4-tetrakis (4-hydroxyphenyl) butane:

25.0 g of succinealdehyde sodium bisulfite, 38.3 g of phenol and 50 ml of acetic acid were applied into 300 ml flask, then 100 ml of the mixture of concentrated sulfuric acid and phosphoric acid (volumetric ratio 3:1) was fed dropwise with stirring over 2 hours at the titration temperature of 0°-2° C. Following that, the solution was stirred for 4 hours at 0° C. The reaction mixture was poured into 600 ml of ice-water, then the temperature of the solution was raised to 70° C. to collect the deposited solid by filtration. The solid was recrystallized from dioxane, then dried under vacuum at 100° C., affording 7.0 g of whitish powder. The yield was 18.1%. The powder was identified as 1,1,5,5-tetrakis(4-hydroxyphenyl)pentane by means of both infrared spectrum and NMR spectrum. The chart of each measurement was shown in FIG. 40 and FIG. 41.

EXAMPLE 17

Sample: Preparation of A-32 through A-68

(1) The clathrate compounds of which guest compound is methanol, ethanol, 2-propanol, acetonitrile, acetone, THF, 1,4-dioxane, benzaldehyde, diethylamine, pyridine or benzene were prepared by using tetrakisphenol obtained in the synthetic Example 1-1 through 1-6 as host compound. For the preparation of clathrate compounds, 2.5 mmol of host compound was added into 10 ml of guest compound and the mixture was stirred for 1 to 300 minutes in the temperature range from 25 to 100° C. Then the solution was immediately filtered and the filtrate was allowed to stand at room temperature for 1 to 48 hours to deposit the crystals. The crystals were collected by filtration, then dried under vacuum at room temperature, affording the clathrate compound specified in the present invention.

The identification of the clathrate compounds were carried out by using TG-DTA measurement and infrared spectrum. The manufacturing condition of the clathrate compounds of the Examples of the present application, guest/host mol ratio determined by TG-DTA measurement of the clathrate compounds and the releasing temperature of the guest compounds were summarized in Table 5.

(2) The clathrate compound of which guest compound is cineole was prepared by using 1,1,2,2-tetrakis(3,5-dimethyl-4-hydroxyphenyl)ethane obtained in the Synthesis Example 1-2 as host compound.

For the preparation of clathrate compounds, 1 mmol of host compound was added into 5 ml of methanol heated to 70° C. and the mixture was stirred until the complete dissolution of the host compound. Then the solution was added to 4 mmol of cineole and stirred for 5 minute at 80° C., then immediately filtered. The filtrate was allowed to stand at room temperature for 24 hours to deposit the crystals. The crystals were collected by filtration, then dried under vacuum at room temperature, affording the clathrate compound specified in the present invention. And the identification of the clathrate compound was carried out by means of TG-DTA measurement. The manufacturing condition of the clathrate compound of the present Examples, guest/host mol ratio determined by TG-DTA measurement of the clathrate compound and the releasing temperature of the guest compounds were summarized in Table 6.

(3) The clathrate compound of which guest compound is hinokithiol, thymol, menthol, citral, eugenol, carbone, geraniol, cineole, menthone or borncol was prepared by using 1,1,2,2-tetrakis(3-methyl-4-hydroxyphenyl)ethane obtained in the synthetic Example 1-2 as host compound.

For the preparation of clathrate compounds, 1 mmol of host compound was added into 5 ml of methanol heated to 60° C. and the mixture was stirred until the complete dissolution of the host compound is made. Then the solution was added to 4 mmol of guest compound and stirred for 5 minute at 60° C., then immediately filtered. The filtrate was allowed to stand at room temperature for 24 hours to deposit the crystals. The crystals were separated by filtration, then dried under vacuum at room temperature, affording the clathrate compound specified in the present invention. And the identifications of the clathrate compounds were carried out by means of TG-DTA measurement. The manufacturing condition of the clathrate compound of the present Example, guest/host mol ratio determined by TG-DTA measurement of the clathrate compound and the releasing temperature of the guest compounds were summarized in Table 7.

EXAMPLE 18

Preparation of Clathrate Compounds 1.1555 g (2.85 mmol) of TEP-DF (Asahi Yukizai Industries) was added into 10 ml of water and the mixture was stirred for 30 min. at 25° C. to make suspension. Then 20 g (11.4 mmol as CMI) of Kathon WT (Rohm & Haas) was gradually fed dropwise thereto and the mixture was stirred for 3 hours to proceed the reaction. Following that, the resulting precipitation was filtered with suction and the filtrate was dried under vacuum at room temperature, affording the sample in pale yellowish powder A-69.

EXAMPLE 19

1.1355 g of TEP-DF was added into 10 ml of water and the mixture was stirred for 20 min. at 50° C. and dispersed. Then 20 g of Kathon WT was gradually fed dropwise thereto and the mixture was reacted under stirring for 3 hours. Following that, the solution was cooled to room temperature, then the resulting precipitation was filtered with suction and dried under vacuum at room temperature, affording the sample in pale yellowish powder A-70.

EXAMPLE 20

1.1355 g (2.85 mmol) of TEP-DF was added into 5 ml of methanol and the mixture was stirred under heating until TEP-DF completely dissolve in the solution. After cooling the solution to 25° C., 20 g of kathon WT was gradually fed dropwise thereto, then the mixture was allowed to stand at reaction for 1 hours. Following that, the resulting deposit was filtered with suction and the filtrate was dried under vacuum at room temperature, affording the sample in pale yellowish crystals A-71.

EXAMPLE 21

1.1355 g (2.85 mmol) of TEP-DF was added into 5 ml of methanol and the mixture was stirred under heating until TEP-DF completely dissolve in the solution. During maintaining the solution at 40° C., 20 g of kathon WT was gradually fed dropwise thereto, then the mixture was allowed to stand at reaction for 15 min. at 40° C. Following that, the solution was cooled to room temperature to result the deposit. The deposit was filtered with suction and the filtrate was dried under vacuum at room temperature, affording the sample in pale yellowish crystals A-72.

COMPARATIVE EXAMPLE 1

0.827 g (2.85 mmol) of β-dinaphthol was dissolved in 17 ml of methanol, then 5.04 g (0.368 g as CMI, 2.86 mmol) of kathon WT was added thereto and stirred, thereby dark substance was deposited. The substance was filtered with suction and dried under vacuum, affording the comparative sample C-1.

Note: The analytical value of the water-soluble fungicide (Kathon WT) used in the Example 1 through 4 and Comparative Example 1. is as follows.

CMI: 10.1 wt %
MI: 3.8 wt %
Rest: Magnesium chloride plus Magnesium nitrate plus water The conditions for preparing the samples of clathrate compounds A-69 through A-72 obtained as described above and the comparative sample of clathrate compound C-1, the included quantity of CMI and MI and the releasing temperature of the guest compounds were shown in Table 8.

The formation of included component was confirmed on each sample of clathrate compound based on the analysis by infrared spectrum, NMR spectrum, X-ray diffraction, DTA, HPLC and TLC. By using X-ray microanalyzer, it was confirmed that all of the clathrate compounds contains neither Magnesium chloride nor Magnesium nitrate.

Figure 48:
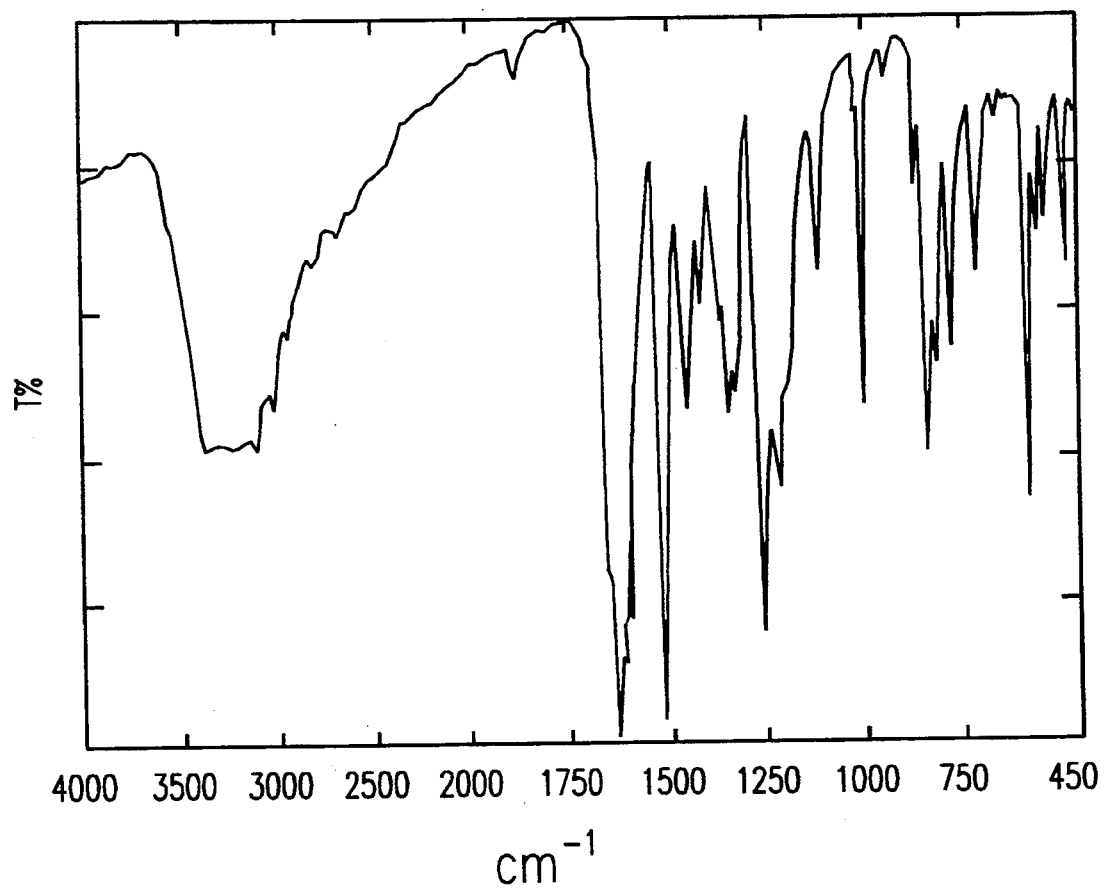
FIG. 48 is a diagram of an infrared spectrum of the sample of clathrate compound A-71.

For the release test of CMI, each of the obtained sample A-71, the comparative sample C-1 and CMI was applied into cellulose dialysis membrane at the rate of 10 mg in conversion to CMI, then the membrane was immersed in pure water 1l. The periodical change in the amount releasing CMI was checked by determining the released amount of CMI after the prescribed time by using elution tester under stirring at the speed of 100 rpm. The results were summarized in Table 9 and the release curve was shown in FIG. 48.

Figure 49:
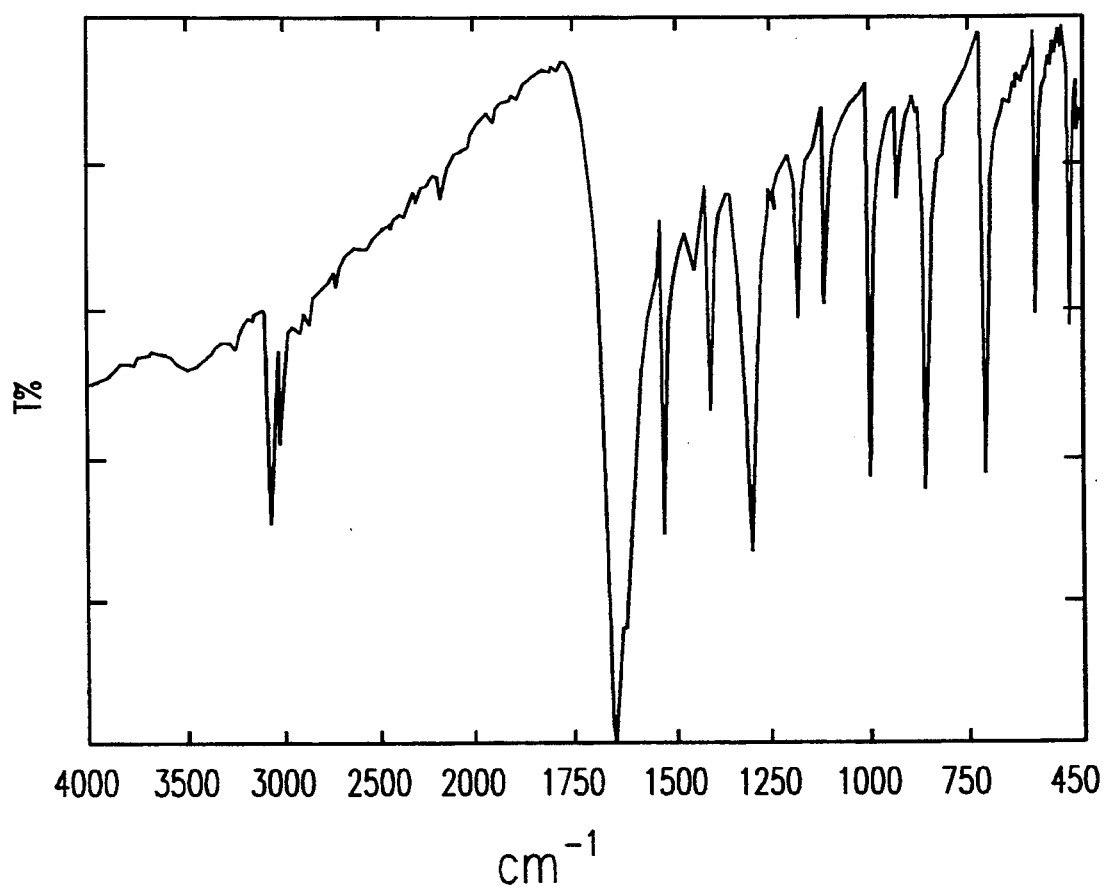
FIG. 49 shows a diagram of an infrared spectrum of CMI isolated from the guest compound, water soluble disinfectant (Kathon WT).
Figure 50:
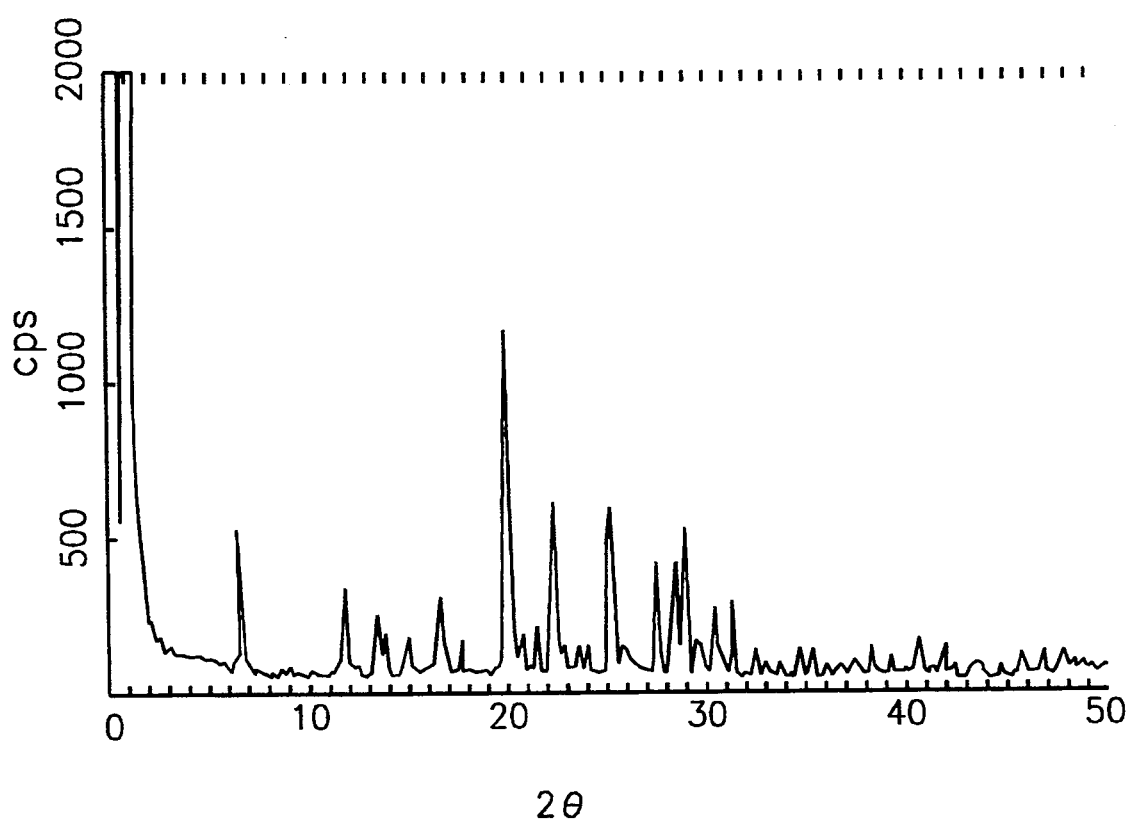
FIG. 50 shows a X-ray diffraction diagram of the clathrate compound sample A-71.
Figure 51:
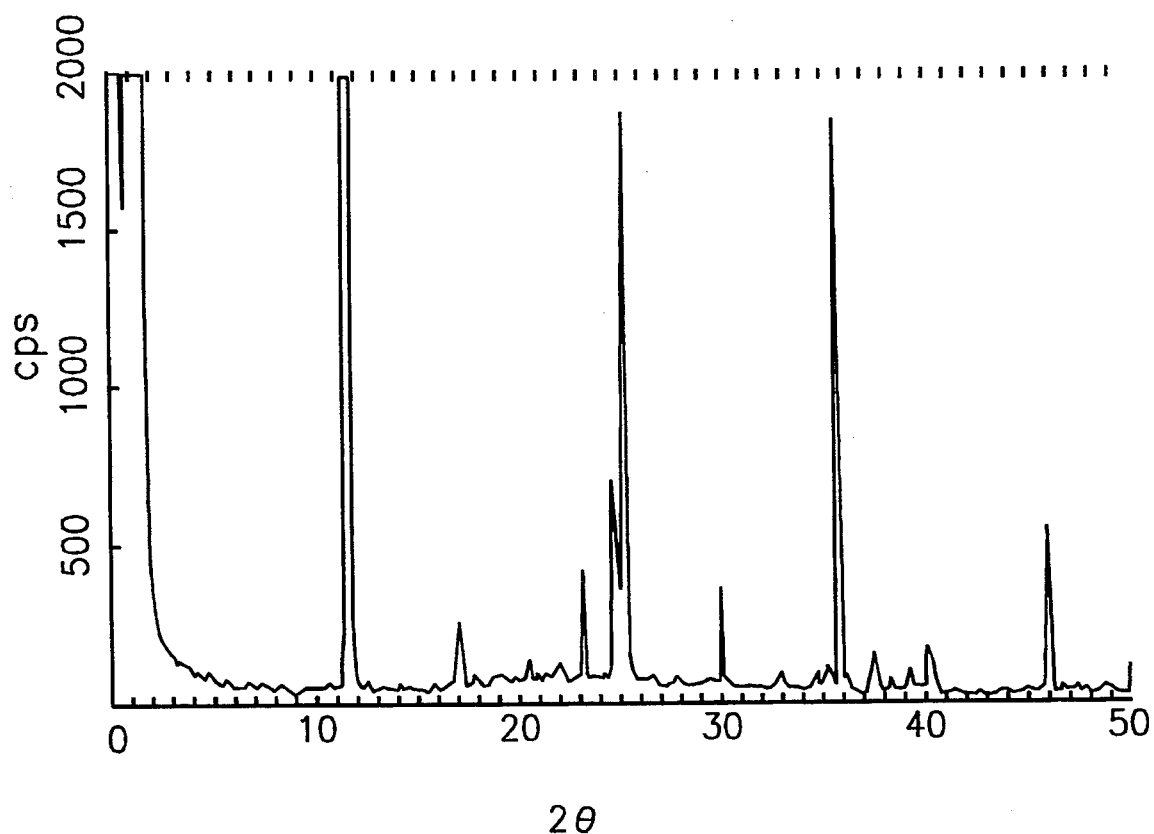
FIG. 51 shows a X-ray diffraction diagram of CMI isolated from the guest compound, water soluble disinfectant (Kathon WT).
Figure 52:
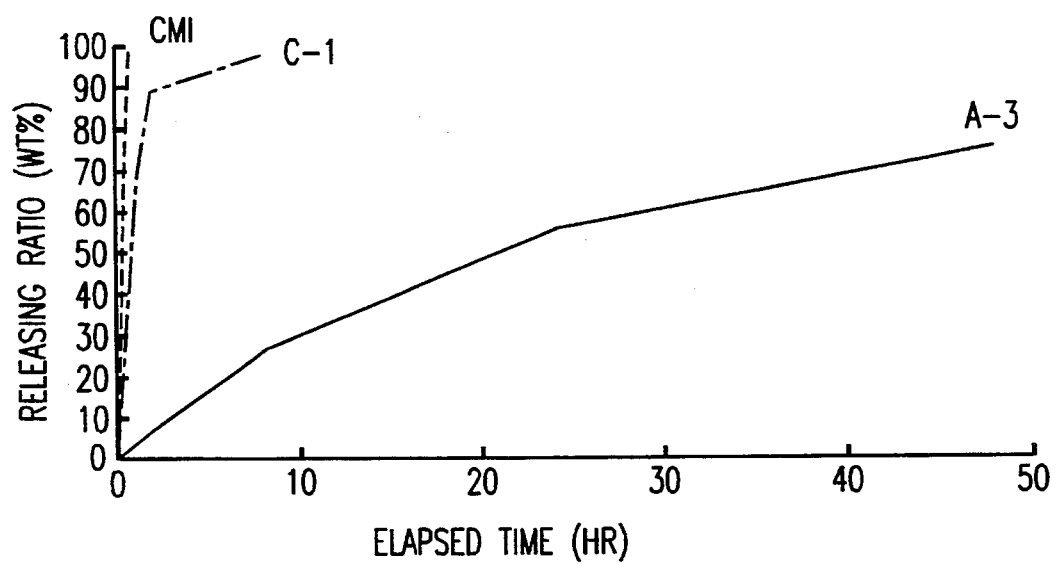
FIG. 52 shows respective release curve of obtained sample A-71, sample for comparison C-1 and CMI obtained from the release amount measured at the release tests.

Furthermore, the infrared spectrums of CMI isolated from the sample of the clathrate compound A-71 obtained in this invention and the guest water-soluble disinfectant (Kathon WT) are shown in FIGS. 49 and 50 respectively and the diagrams of X-ray diffraction of them are shown in FIGS. 51 and 52 respectively.

INDUSTRIAL APPLICABILITY

The novel clathrate compounds of which host compound is tetrakisphenol specified in the present invention have the following characteristics.

1) Wide range of organic compounds such as alcohols, ethers, esters, ketones, BTX solvents including benzene and the like, fungicides, heterocyclic compounds containing nitrogen, essential oils, perfumes and the like can be included extremely easily as guest compound.
2) By the inclusion of the compounds having the boiling point near ordinary temperature, the control of volatilization and transpiration can be made.
3) It makes possible to recover the organic compound contaminated in water selectively as included component.
4) It makes possible to recover the desired compound selectively as included component from the mixture of organic compounds which may not be separated by distillation or other means because of having similar boiling points.
5) It makes possible to separate and recover the compound included as guest compound by easily releasing them by heating and the like.
6) As included component is solid under ordinary temperature, it can be press to form tablets and it is very easy for handling.
7) When take CMI, of which toxicity and skin irritation activity are high and which is a disinfectant for industrial use, as guest compound and use the compound having lower toxicity such as tetrakis(hydroxyphenyl)ethanes as host, the toxicity and the skin irritation action can be deteriorated because CMI is included with low toxic host compound. Further, since CMI as active ingredient is released at appropriate period in aqueous system, it is useful for the disinfectant for circulatory toilet of train which is exchanged every 2–3 days. Moreover, as host compound protects CMI as active ingredient, the deterioration of the antimicrobial activity resulted from the reaction of CMI with other substances can be prevented.

As illustrated above, the present invention relates to the clathrate compounds which can include wide range of organic compounds, and has an object to provide easy handling novel clathrate compounds and process for the preparation thereof which may be significant for contributing the industries.

TABLE 1

| | Host | | | Reaction Condition | | Clathlate Compound | |
| Sample | Compound | Solvent | Guest Compound | Temp. (C.°) | Time (min.) | Guest/Host (mol ratio) | Guest releasing temperature (C.°) |
| --- | --- | --- | --- | --- | --- | --- | --- |
| A-1 | TEP-DF[1)] | Methanol | Methanol | 50 | 5 | 1.9 | 81~102 |
| A-2 | TEP-DF[1)] | Ethanol | Ethanol | 60 | 5 | 3.7 | 69~100 |
| A-3 | TEP-DF[1)] | i-Propanol | i-Propanol | 65 | 10 | 2.3 | 70~90 |
| A-4 | TEP-DF[1)] | Benzaldehyde | Benzaldehyde | 120 | 5 | 1.8 | 98~124 |

TABLE 1-continued

| Sample | Host Compound | Solvent | Guest Compound | Reaction Condition Temp. (C.°) | Time (min.) | Clathlate Compound Guest/Host (mol ratio) | Guest releasing temperature (C.°) |
|---|---|---|---|---|---|---|---|
| A-5 | TEP-DF[1] | Methanol:Water = 1:1[2] | Methanol | 55 | 10 | 2.0 | 82~99 |
| A-6 | TEP-DF[1] | Ethanol:Water = 1:1[2] | Ethanol | 65 | 10 | 1.5 | 52~72 |
| A-7 | TEP-DF[1] | Acetone | Acetone | 56 | 3 | 1.9 | 103~124 |
| A-8 | TEP-DF[1] | Acetaldehyde | Acetaldehyde | 22 | 60 | 1.0 | 99~113 |
| A-9 | TEP-DF[1] | Tetrahydrofuran | Tetrahydrofuran | 65 | 4 | 3.0 | 79~101 |
| A-10 | TEP-DF[1] | Acetonitrile | Acetonitrile | 82 | 3 | 2.0 | 106~127 |
| A-11 | TEP-DF[1] | Acetonitrile: i-Propanol = 1:1[2] | Acetonitrile | 82 | 10 | 1.9 | 111~132 |
| A-12 | TEP-DF[1] | n-Propanol/Water | n-Propanol | 80 | 10 | 1.1 | 56.9 |
| A-13 | TEP-DF[1] | Ethyl acetate | Ethyl acetate | 60 | 10 | 2.0 | 69.7 |
| A-14 | TEP-DF[1] | 1,4-dioxane | 1,4-dioxane | 90 | 10 | 3.9 | 101.1 |
| A-15 | TEP-DF[1] | Diethylamine | Diethylamine | 50 | 20 | 2.0 | 119.1 |
| A-16 | TEP-DF[1] | Triethylamine | Triethylamine | 80 | 20 | 0.9 | 115.5 |
| A-17 | TEP-DF[1] | Benzimidazole[3] | Benzimidazole | 50 | 10 | 2.0 | 157.6 |
| A-18 | TEP-DF[1] | Benzimidazole[4] | Benzimidazole | 80 | 10 | 2.0 | 163.5 |

Note)
[1]:1,1,2,2,-tetrakis(p-hydroxyphenyl)ethane
[2]:Volumetric ratio
[3]:Solvent:+Methanol
[4]:Solvent:+isopropanol

TABLE 2

| Sample No. | Host Compound | Guest Compound | Solvent | Condition for Reaction Temp. (C.°) | Time (min.) | Clathlate Compound Guest/Host (mol ratio) | Guest releasing temperature (°C.) |
|---|---|---|---|---|---|---|---|
| A-19 | TEP-DF[1] | pyridine | methanol | 60 | 10 | 3.9 | 111.5 |
| A-20 | TEP-DF[1] | pyrrole | methanol | 60 | 10 | 2.0 | 137. |
| A-21 | TEP-DF[1] | pyrrole | isopropanol | 80 | 30 | 2.2 | 137.7 |
| A-22 | TEP-DF[1] | pyrazine | methanol | 60 | 20 | 1.3~1.6 | 76.8 |
| A-23 | TEP-DF[1] | pyrazole | methanol | 60 | 20 | 2.9 | 86.3 |
| A-24 | TEP-DF[1] | imidazole | methanol | 60 | 20 | 1.3~1.6 | 103.8 |
| A-25 | TEP-DF[1] | 1,2,4-triazole | methanol | 60 | 20 | 1.8~2.0 | 159.5 |
| A-26 | TEP-DF[1] | pyridine | — | Room temp. | 3 | 3.9 | 102.9 |
| A-27 | TEP-DF[1] | pyrrole | — | Room temp. | 5 | 0.9 | 99.9 |

Note)
[1]:1,1,2,2,-tetrakis(p-hydroxyphenyl)ethane

TABLE 3

| Sample No. | Host compound | Guest compound | Solvent | Condition for reaction Temp. (°C.) | Time (min.) | Clathrate compound Guest/Host (mol ratio) | Guest releasing temperature (°C.) |
|---|---|---|---|---|---|---|---|
| A-28 | TEP-DF[1] (1.0 g) | 1.8-cineole (1.55 g) | methanol (5 ml) | 60 | 10 | 4.0 | 102.9 |
| A-29 | TEP-DF[1] (1.0 g) | hinokithiol (1.65 g) | methanol (5 ml) | 60 | 10 | 4.0 | 151.6 |
| A-30 | TEP-DF[1] (1.0 g) | l-menthol (1.57 g) | benzene (5 ml) | 40 | 30 | 2.5 | 98.6 |
| A-31 | TEP-DF[1] (1.0 g) | α-terpineol (1.55 g) | — | 60 | 5 | 4.0 | 80.5 |

Note)
[1]:1,1,2,2,-tetrakis(p-hydroxyphenyl)ethane
( ):Amount used at the reaction.

TABLE 4

| Sample No. | Samples | Temperature at test (C.°) | Time (day) 1 | 2 | 4 | 4 | 8 | 12 | 18 |
|---|---|---|---|---|---|---|---|---|---|
| A-28 | 1,8-cineole-included compound | 25 | 0.1 | 0.3 | 0.6 | 0.9 | 1.2 | 2.0 | 2.9 |
| R-1 | 1,8-cineole | | 24 | 49 | 100 | — | — | — | — |
| A-28 | 1,8-cineole-included compound | 40 | 4 | 9 | 21 | 32 | 45 | 68 | 99 |
| R-1 | 1,8-cineole | | 71 | 100 | — | — | — | — | — |
| A-29 | hinokithiol-included compound | 40 | 0.1 | 0.1 | 0.2 | 0.4 | 0.5 | 0.6 | 0.8 |
| R-2 | hinokithiol | | 0.3 | 0.5 | 1.1 | 2.0 | 2.2 | 3.0 | 4.2 |

Note)
Temperature indicated is that on the day elapsed (day).

TABLE 5

| Sample No. | Host | Guest compound | Temp. stirred °C. | Time stirred min. | Time remained Hr |
|---|---|---|---|---|---|
| A-32 | 1-1 | 1,4-dioxane | 80 | 5 | 24 |
| A-33 | 1-1 | benzaldehyde | 100 | 10 | 24 |
| A-34 | 1-1 | benzene | 50 | 10 | 24 |
| A-35 | 1-2 | methanol | 50 | 5 | 24 |
| A-36 | 1-2 | ethanol | 60 | 5 | 24 |
| A-37 | 1-2 | 2-propanol | 25 | 300 | 1 |
| A-38 | 1-2 | acetonitrile | 60 | 5 | 24 |
| A-39 | 1-2 | acetone | 50 | 5 | 24 |
| A-40 | 1-2 | THF | 50 | 5 | 24 |
| A-41 | 1-2 | 1,4-dioxane | 80 | 10 | 24 |
| A-42 | 1-2 | diethylamine | 50 | 1 | 24 |
| A-43 | 1-2 | triethylamine | 70 | 1 | 24 |
| A-44 | 1-2 | pyridine | 80 | 10 | 24 |
| A-45 | 1-2 | benzene | 70 | 5 | 21 |
| A-46 | 1-3 | acetonitrile | 60 | 5 | 48 |
| A-47 | 1-3 | acetone | 50 | 5 | 24 |
| A-48 | 1-3 | THF | 50 | 5 | 24 |
| A-49 | 1-3 | pyridine | 80 | 10 | 24 |
| A-50 | 1-4 | 1,4-dioxane | 80 | 10 | 24 |
| A-51 | 1-5 | 2-propanol | 70 | 5 | 48 |
| A-52 | 1-5 | acetonitrile | 60 | 5 | 48 |
| A-53 | 1-5 | THF | 50 | 5 | 48 |
| A-54 | 1-5 | 1,4-dioxane | 80 | 10 | 48 |
| A-55 | 1-6 | THF | 50 | 5 | 48 |
| A-56 | 1-6 | 1,4-dioxane | 80 | 10 | 48 |

TABLE 6

| Sample No. | Host | Guest compound | Guest/Host mol ratio | Guest boiling point | Releasing tmep. °C. |
|---|---|---|---|---|---|
| A-57 | 1-1 | cineole | 2.0 | 170 | 75.8 |

TABLE 7

| Sample No. | Host | Guest compound | Guest/Host mol ratio | Guest boiling point | Releasing tmep. °C. |
|---|---|---|---|---|---|
| A-58 | 1-2 | hinokthiol | 2.1 | 141 | 71.1 |
| A-59 | 1-2 | thymol | 0.8 | 233 | 78.9 |
| A-60 | 1-2 | menthol | 0.6 | 215 | 47.9 |
| A-61 | 1-2 | citral | 0.9 | 228 | 111.4 |
| A-62 | 1-2 | eugenol | 0.3 | 253 | 70.5 |
| A-63 | 1-2 | carvone | 2.0 | 231 | 110.8 |
| A-64 | 1-2 | geraniol | 1.0 | 230 | 89.3 |
| A-65 | 1-2 | cineole | 3.1 | 170 | 63.4 |
| A-66 | 1-2 | menthone | 2.0 | 207 | 86.5 |
| A-67 | 1-2 | borneol | 1.2 | 214 | 63.0 |

TABLE 8

| Sample No. | Host compound | Guest compound | Solvent for reaction | Reaction Condition Temp °C. | Reaction Condition Time min | Guest/Host (mol ratio) CMI | Guest/Host (mol ratio) MI | Guest releasing temperature (°C.) |
|---|---|---|---|---|---|---|---|---|
| Example | | | | | | | | |
| A-69 | TEP-DF | Kathon WT | — | 25 | 180 | 1.16 | 0.02 | 152 |
| A-70 | TEP-DF | Kathon WT | — | 50 | 30 | 1.21 | 0.02 | 155 |
| A-71 | TEP-DF | Kathon WT | methanol | 25 | 60 | 1.96 | 0.02 | 168 |
| A-72 | TEP-DF | Kathon WT | methanol | 40 | 15 | 1.91 | 0.02 | 167 |
| Comparative Example | | | | | | | | |
| C-1 | β-dinaphthol | Kathon WT | methanol | 25 | 60 | 0.95 | 0.04 | — |

TABLE 9

| | Sample No. | Released ratio of CMI in the Sample (Weight %) Time elapsed (hour) | | | | | |
|---|---|---|---|---|---|---|---|
| | | 0.25 | 0.5 | 1 | 2 | 24 | 48 |
| Present Invention | A-71 | 1 | 2 | 4 | 8 | 57 | 76 |
| Comparative Example | C-1 | 14 | 33 | 69 | 90 | — | — |
| | CMI | 69 | 100 | — | — | — | — |

{Note}
A-3: Sample A-3 synthesized in Example 3.
C-1: Sample C-1 synthesized in Comparative Example 1.
CMI: 5-chloro-2-methyl-4-isothiazoline-3-one (water-soluble disinfectant, Tradename: Kathon WT, Rohm & Haas Limited).

What is claimed is:

1. Clathrate compound prepared by the method of reacting tetrakisphenol of the formula

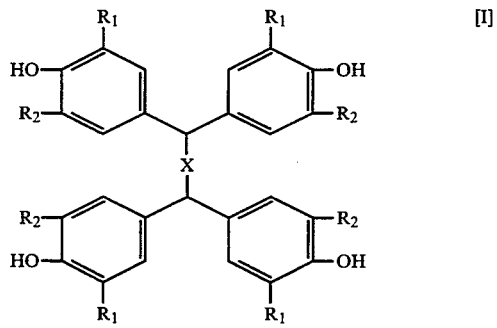

wherein X represent $(CH_2)_n$, n is 0, 1, 2, or 3, and $R_1$ and $R_2$ are the same or different and each are hydrogen, an alkyl group having 1 to 4 carbon atoms, a phenyl group, halogen or alkoxy group having 1 to 4 atoms; and, an organic compound under conditions sufficient to form the clathrate compound having the tetrakisphenol as the host.

2. Clathrate compound prepared according to the method of claim 1, wherein the organic compound is selected from the group comprising methanol, ethanol, i-propanol, n-butanol, 2-ethylhexanol, formaldehyde, acetaldehyde, benzaldehyde, acetone, methylethylketone, acetonitrile, tetrahydrofuran, diethylether, methyl acetate, ethyl acetate, butyl acetate, cineole, hinokithiol, menthol, menthone, terpineol, borneol, nopol, citral, citrinellol, citronellal, geraniol, linalool, thymol, carvone, eugenol, dimethyloctanol, fragrant orange-colored olive, jasmine, lemon oil, pyridine, pyrrole, imidazole, pyrazine, pyrazole, 1,2,4-triazole, thiazole, pyrrolidine, imidazoline, pyrroline, oxazole, piperine, pyrimidine, pyridazine, triazine and 5-chloro-2-methyl-4-isothiazoline-3-one.

3. Clathrate compound prepared according to the method of claim 2 wherein the organic compound is selected from the group comprising cineole, hinokithiol, menthol, menthone, terpineol, borneol, nopol, citral, citrinellol, citronellal, geraniol, linalool, thymol, carvone, eugenol, dimethyloctanol, fragrant orange-colored olive, jasmine, lemon oil, pyridine, pyrrole, imidazole, pyrazine, pyrazole, 1,2,4-triazole, thiazole, pyrrolidine, imidazoline, pyrroline, oxazole, piperine, pyrimidine, pyridazine, triazine and 5-chloro-2-methyl-4-isothiazoline-3-one.

4. Clathrate compound prepared according to the method of claim 1 wherein the tetrakisphenol is 1,1,2,2-tetrakis (4-hydroxyphenyl)ethane.

5. Clathrate compound prepared according to the method of claim 2 wherein the tetrakisphenol is 1,1,2,2-(4-hydroxyphenyl)ethane.

6. Clathrate compound wherein the host compound comprises tetrakisphenol of the formula

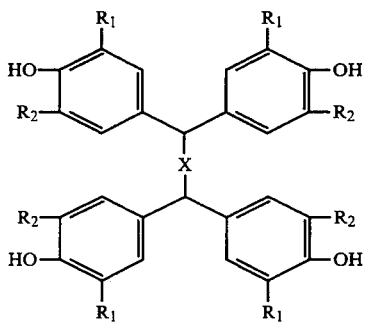

[I]

wherein X represent $(CH_2)_n$, n is 0, 1, 2, or 3, and $R^1$ and $R^2$ are the same or different and each are hydrogen, lower alkyl, optionally substituted phenyl, halogen or lower alkoxy; and the guest compound comprises an organic compound.

7. Clathrate compound according to claim 6 wherein the guest compound is selected from the group comprising methanol, ethanol, i-propanol, n-butanol, 2-ethylhexanol, formaldehyde, acetaldehyde, benzaldehyde, acetone, methylethylketone, acetonitrile, tetrahydrofuran, diethylether, methyl acetate, ethyl acetate, butyl acetate, cineole, hinokithiol, menthol, menthone, terpineol, borneol, nopol, citral, citrinellol, citronellal, geraniol, linalool, thymol, carvone, eugenol, dimethyloctanol, fragrant orange-colored olive, jasmine, lemon oil, pyridine, pyrrole, imidazole, pyrazine, pyrazole, 1,2,4-triazole, thiazole,-pyrrolidine, imidazoline, pyrroline, oxazole, piperine, pyrimidine, pyridazine, triazine and 5-chloro-2-methyl-4-isothiazoline-3-one.

8. Clathrate compound according to claim 7 wherein the guest compound is selected from the group comprising cineole, hinokithiol, menthol, menthone, terpineol, borneol, nopol, citral, citrinellol, citronellal, geraniol, linalool, thymol, carvone, eugenol, dimethyloctanol, fragrant orange-colored olive, jasmine, lemon oil, pyridine, pyrrole, imidazole, imidazoline, pyrroline, oxazole, piperine, pyrimidine, pyridazine, triazine and 5-chloro-2-methyl-4-isothiazoline-3-one.

9. Clathrate compound according to claim 6 wherein the host compound is 1,1,2,2-(4-hydroxyphenyl)ethane.

10. Clathrate compound according to claim 7 wherein the host compound is 1,1,2,2-(4-hydroxyphenyl)ethane.

11. Clathrate compound prepared by the method of claim 1 wherein the conditions include a temperature from 22° C. to 100° C. and a time from 3 minutes to 300 minutes.

* * * * *